United States Patent
Kurihara et al.

(10) Patent No.: US 11,318,185 B2
(45) Date of Patent: May 3, 2022

(54) IMMUNOGENIC PEPTIDES OF SCD1 PROTEIN

(71) Applicant: TORAY INDUSTRIES, INC., Tokyo (JP)

(72) Inventors: Akira Kurihara, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 130 days.

(21) Appl. No.: 16/080,857

(22) PCT Filed: Mar. 1, 2017

(86) PCT No.: PCT/JP2017/008055
§ 371 (c)(1),
(2) Date: Aug. 29, 2018

(87) PCT Pub. No.: WO2017/150595
PCT Pub. Date: Sep. 8, 2017

(65) Prior Publication Data
US 2019/0076505 A1   Mar. 14, 2019

(30) Foreign Application Priority Data

Mar. 2, 2016 (JP) .............................. JP2016-040364

(51) Int. Cl.
| | |
|---|---|
| *A61K 38/17* | (2006.01) |
| *A61K 38/43* | (2006.01) |
| *A61K 35/15* | (2015.01) |
| *A61K 38/08* | (2019.01) |
| *A61K 35/76* | (2015.01) |
| *A61K 38/00* | (2006.01) |
| *A61K 45/00* | (2006.01) |
| *A61P 35/00* | (2006.01) |
| *C12N 15/62* | (2006.01) |
| *C12N 9/24* | (2006.01) |

(52) U.S. Cl.
CPC .......... *A61K 38/1774* (2013.01); *A61K 35/15* (2013.01); *A61K 35/76* (2013.01); *A61K 38/00* (2013.01); *A61K 45/00* (2013.01); *A61P 35/00* (2018.01); *C12N 15/62* (2013.01); *A61K 38/005* (2013.01); *C12N 9/248* (2013.01)

(58) Field of Classification Search
CPC combination set(s) only.
See application file for complete search history.

(56) References Cited

U.S. PATENT DOCUMENTS

| | | |
|---|---|---|
| 8,053,633 B1 | 11/2011 | Hildebrand et al. |
| 2004/0226056 A1 | 11/2004 | Roch et al. |
| 2013/0096181 A1 | 4/2013 | Ashkenazi et al. |
| 2014/0154206 A1* | 6/2014 | Kurihara ................ A61K 38/21 424/85.2 |

FOREIGN PATENT DOCUMENTS

| | | | |
|---|---|---|---|
| EP | 2711015 A1 | | 3/2014 |
| JP | 2015-501301 A | | 1/2015 |
| WO | WO 2009/090651 | * | 7/2009 |
| WO | WO 2009/090651 A2 | | 7/2009 |
| WO | WO 2012/157736 A1 | | 11/2012 |
| WO | WO 2016/081947 A2 | | 5/2016 |
| WO | WO 2016/172722 A1 | | 10/2016 |
| WO | WO 2017/184590 A1 | | 10/2017 |

OTHER PUBLICATIONS

Extended European Search Report, dated Jul. 11, 2019, for European Application No. 17760059.0.
Bai et al., "X-ray structure of a mammalian stearoyl-CoA desaturase", Nature, vol. 524, No. 7564, Aug. 13, 2015, pp. 252-267.
International Search Report (PCT/ISA/210) issued in PCT/JP2017/008055, dated Mar. 28, 2017.
Written Opinion (PCT/ISA/237) issued in PCT/JP2017/008055, dated Mar. 28, 2017.

* cited by examiner

*Primary Examiner* — Laura B Goddard
(74) *Attorney, Agent, or Firm* — Birch, Stewart, Kolasch & Birch, LLP

(57) ABSTRACT

The present invention addresses the problem of finding a novel peptide useful as an active ingredient in an agent for treating or preventing cancer, and to provide the use of the polypeptide as an immune inducer.
The immune inducer containing as an active ingredient: (a) a polypeptide consisting of any one of the amino acid sequences represented by SEQ ID NOs: 3 to 45; or (b) a polypeptide comprising one to several amino acid deletions, substitutions or additions in the amino acid sequence of the polypeptide (a); is useful as an agent for treating or preventing cancer, etc.

8 Claims, 8 Drawing Sheets

Specification includes a Sequence Listing.

IMMUNOGENIC PEPTIDES OF SCD1 PROTEIN

TECHNICAL FIELD

The present invention relates to a novel immune inducer useful as an active ingredient in an agent for treating or preventing cancer.

BACKGROUND ART

The SCD1 (stearoyl-coA desaturase 1) protein is a protein that introduces a double bond at the C9-C10 position of a saturated fatty acid.

SCD1 protein is suggested to be associated with the development of cancer. For example, according to Non-Patent Literature 1 and 2, its expression has increased in various cancers such as liver cancer, esophageal cancer and colorectal cancer. It is disclosed that the inhibition of the function of SCD1 by way of siRNA and a small molecule inhibitor compound prevents the proliferation of cancer cells and induces the apoptosis and thus shrinkage of the formed tumor.

On the other hand, Patent Literature 1 discloses that the SCD1 protein has an immune-inducing activity against cancer cells, and thus are useful for treatment and/or prevention of cancer. However, Patent Literature 1 does not disclose peptides that bind to MHC molecules.

CITATION LIST

Patent Literature

Patent Literature 1: WO 2012/157736

Non-Patent Literature

Non-Patent Literature 1: Igal R A. Carcinogenesis. September; 31 (9): 1509-15 (2010)
Non-Patent Literature 2: Chen L. Sci. Rep. 6, 19665 (2016)

SUMMARY OF INVENTION

Technical Problem

An object of the present invention is to find a novel polypeptide useful as an active ingredient in an agent for treating or preventing cancer, and to provide the use of the polypeptide as an immune inducer.

Another object of the present invention is to provide an isolated antigen-presenting cell including a complex of the polypeptide and an MHC molecule, and an isolated T cell which selectively binds to a complex of the polypeptide and an MHC molecule, as well as an agent for treating or preventing cancer including the same.

Solution to Problem

As a result of intensive research, the present inventors have found that the human SCD1 protein consisting of the amino acid sequence represented by SEQ ID NO: 2 is specifically expressed in tissues or cells of malignant lymphoma, breast cancer, liver cancer, prostate cancer, ovarian cancer, renal cancer, colorectal cancer, stomach cancer, malignant brain tumor, esophageal cancer, and lung cancer. Further, the inventors have found out that a partial peptide present in a specific region of the SCD1 protein has an ability (immune-inducing activity) to activate and propagate T cells specific to the polypeptide via the presentation by the antigen-presenting cells, and that the immune-inducing activity is useful for the treating or preventing cancer. Based on these findings, the inventors have found out that the polypeptide can be used as an active ingredient in an immune inducer for treating and/or preventing cancer, and that antigen-presenting cells which have been in contact with the peptide, and T cells which have been in contact with the antigen-presenting cells are also useful in the treatment or prevention of cancer, thereby completing the present invention.

Specifically, the present invention has the following characteristics (1) to (12).

(1) An immune inducer comprising, as an active ingredient, at least one polypeptide having an immune-inducing activity and selected from the group of polypeptides (a) or (b) below:
 (a) polypeptides consisting of 7 or more consecutive amino acids within the region of positions 34 to 50, positions 69 to 148, positions 178 to 195, positions 207 to 242, positions 247 to 280 and positions 296 to 332 in the amino acid sequence represented by SEQ ID NO: 2;
 (b) polypeptides comprising one to several amino acid deletions, substitutions, insertions or additions in the amino acid sequence of any one of the polypeptides (a); or
 a recombinant vector comprising at least one polynucleotide encoding any one of the polypeptides, and capable of expressing the polypeptide in vivo.
(2) The immune inducer according to (1), wherein the polypeptide having an immune-inducing activity binds to an MHC class I molecule.
(3) The immune inducer according to (2), wherein the polypeptide having an immune-inducing activity is any one of the polypeptides selected from the group of polypeptides (c) to (e) below:
 (c) polypeptides consisting of the amino acid sequences represented by SEQ ID NOs: 3 to 36;
 (d) polypeptides comprising one to several amino acid deletions, substitutions, insertions or additions in the amino acid sequence of any one of the polypeptides (c);
 (e) polypeptides each comprising as a partial sequence any one of the polypeptides (c) or (d).
(4) The immune inducer according to (1), wherein the polypeptide having an immune-inducing activity binds to an MHC class II molecule.
(5) The immune inducer according to (4), wherein the polypeptide having an immune-inducing activity is any one of the polypeptides selected from the group of polypeptides (f) to (h) below:
 (f) polypeptides consisting of the amino acid sequences represented by SEQ ID NOs: 37 to 45;
 (g) polypeptides comprising one to several amino acids deletions, substitutions, insertions or additions in the amino acid sequence of any one of the polypeptides (f);
 (h) polypeptides each comprising as a partial sequence any one of the polypeptides (f) or (g).
(6) The immune inducer according to any one of (1) to (5), which is used as an active ingredient in an agent for treating or preventing cancer.
(7) The immune inducer according to (6), wherein the cancer is a cancer expressing SCD1 protein.
(8) The immune inducer according to (6) or (7), wherein the cancer is malignant lymphoma, breast cancer, liver cancer, prostate cancer, ovarian cancer, renal cancer, colorectal cancer, stomach cancer, malignant brain tumor, esophageal cancer or lung cancer.

(9) The immune inducer, according to any one of (1) to (8), further comprising an immune enhancer.

(10) An isolated antigen-presenting cell comprising a complex of the polypeptide having an immune-inducing activity according to (1), (3) or (5) and an MHC molecule.

(11) An isolated T cell which selectively binds to a complex of the polypeptide having an immune-inducing activity according to (1), (3) or (5) and an MHC molecule.

(12) A polypeptide having an immune-inducing activity and selected from the group of polypeptides (a) or (b) below:
(a) polypeptides having an immune-inducing activity and consisting of 7 or more consecutive amino acids within the region of positions 34 to 50, positions 69 to 148, positions 178 to 195, positions 207 to 242, positions 247 to 280 and positions 296 to 332 in the amino acid sequence represented by SEQ ID NO: 2;
(b) polypeptides comprising one to several amino acid deletions, substitutions, insertions or additions in the amino acid sequence of any one of the polypeptides (a).

(13) An agent for treating or preventing cancer comprising, as an active ingredient, one or more selected from the group consisting of (i) to (iv) below:
(i) at least one polypeptide having an immune-inducing activity and selected from the group of polypeptides (a) or (b) below:
 (a) polypeptides consisting of 7 or more consecutive amino acids within the region of positions 34 to 50, positions 69 to 148, positions 178 to 195, positions 207 to 242, positions 247 to 280 and positions 296 to 332 in the amino acid sequence represented by SEQ ID NO: 2,
 (b) polypeptides comprising one to several amino acid deletions, substitutions, insertions or additions in the amino acid sequence of any one of the polypeptides (a);
(ii) a recombinant vector comprising at least one polynucleotide encoding any one of the polypeptides, and capable of expressing the polypeptide in vivo;
(iii) an isolated antigen-presenting cell comprising a complex of any one of the polypeptides and an MHC molecule; and
(iv) an isolated T cell which is specific to any one of the polypeptides.

(14) The agent for treating or preventing cancer according to (13), wherein the polypeptide having an immune-inducing activity is at least one of the polypeptides selected from the group of polypeptides (c) to (h) below:
(c) polypeptides consisting of the amino acid sequences represented by SEQ ID NOs: 3 to 36;
(d) polypeptides comprising one to several amino acid deletions, substitutions, insertions or additions in the amino acid sequence of any one of the polypeptides (c);
(e) polypeptides each comprising as a partial sequence any one of the polypeptides (c) or (d);
(f) polypeptides consisting of the amino acid sequences represented by SEQ ID NOs: 37 to 45;
(g) polypeptides comprising one to several amino acids deletions, substitutions, insertions or additions in the amino acid sequence of any one of the polypeptides (f);
(h) polypeptides each comprising as a partial sequence any one of the polypeptides (f) or (g).

(15) The agent for treating or preventing cancer according to (13) or (14), wherein the cancer is a cancer expressing SCD1 protein.

(16) A method of treating or preventing cancer, comprising administering to a subject animal in need thereof, one or more selected from the group consisting of (i) to (iv) below:
(i) at least one polypeptide having an immune-inducing activity and selected from the group of polypeptides (a) or (b) below:
 (a) polypeptides consisting of 7 or more consecutive amino acids within the region of positions 34 to 50, positions 69 to 148, positions 178 to 195, positions 207 to 242, positions 247 to 280 and positions 296 to 332 in the amino acid sequence represented by SEQ ID NO: 2,
 (b) polypeptides comprising one to several amino acid deletions, substitutions, insertions or additions in the amino acid sequence of any one of the polypeptides (a);
(ii) a recombinant vector comprising at least one polynucleotide encoding any one of the polypeptides, and capable of expressing the polypeptide in vivo;
(iii) an isolated antigen-presenting cell comprising a complex of any one of the polypeptides and an MHC molecule; and
(iv) an isolated T cell which is specific to any one of the polypeptides.

(17) The method according to (16), wherein the polypeptide having an immune-inducing activity is any one of the polypeptides selected from the group of polypeptides (c) to (h) below:
(c) polypeptides consisting of the amino acid sequences represented by SEQ ID NOs: 3 to 36;
(d) polypeptides comprising one to several amino acid deletions, substitutions, insertions or additions in the amino acid sequence of any one of the polypeptides (c);
(e) polypeptides each comprising as a partial sequence any one of the polypeptides (c) or (d);
(f) polypeptides consisting of the amino acid sequences represented by SEQ ID NOs: 37 to 45;
(g) polypeptides comprising one to several amino acids deletions, substitutions, insertions or additions in the amino acid sequence of any one of the polypeptides (f);
(h) polypeptides each comprising as a partial sequence any one of the polypeptides (f) or (g).

(18) The method according to (16) or (17), wherein the cancer is a cancer expressing SCD1 protein.

The present specification encompasses the disclosure of Japanese Patent Application No. 2016-040364 to which the present application claims priority.

Effects of Invention

The present invention provides a novel immune inducer useful as an active ingredient in an agent for treating or preventing cancer.

Further, as specifically shown in Examples to be described later, the polypeptides used in the present invention can induce immune cells that kill cancer cells, thereby enabling the reduction in size or regression of an already existing cancer. In addition, the peptides used in the present invention can also enhance the induction of the immune cells that kill cancer cells, and thereby enabling the reduction in size or regression of an already existing cancer. Therefore, the polypeptides according to the present invention are useful as an active ingredient in an agent for treating or preventing cancer.

Figure 2:
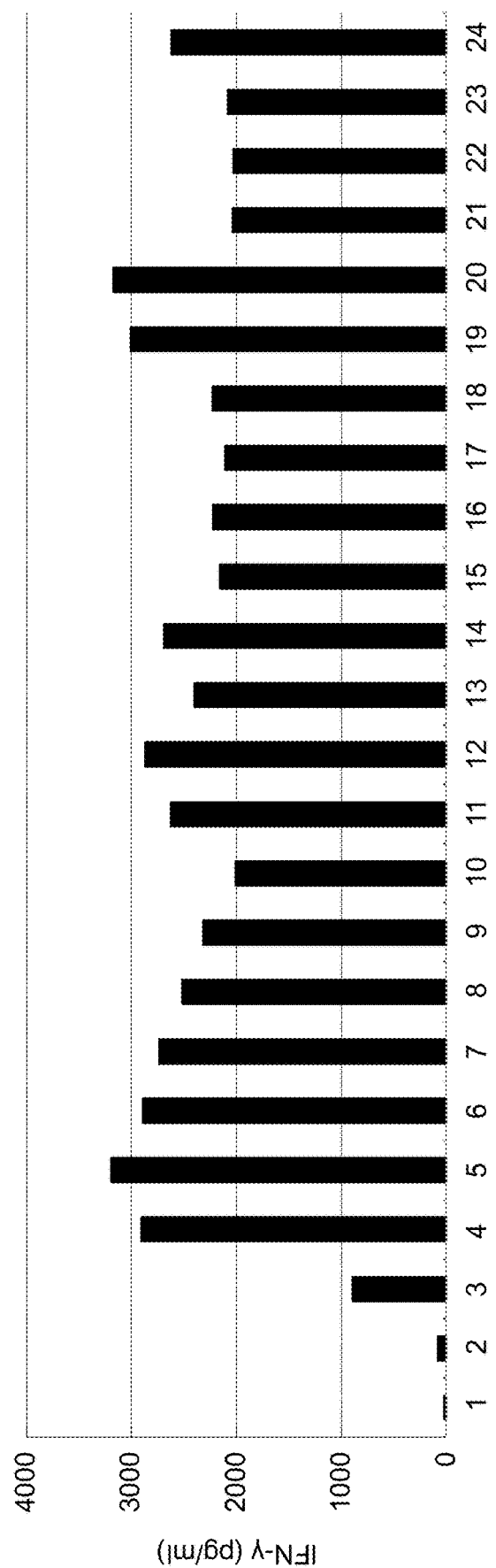

FIG. 2 shows that CD8-positive T cells specific to each of polypeptides consisting of the amino acid sequences represented by SEQ ID NOs: 3 to 23 recognize the complex consisting of the polypeptide and HLA-A0201 and produce IFN-γ. In FIG. 2, Lanes 4 to 24 on the horizontal axis show the IFN-γ-producing abilities of HLA-A0201-positive CD8-positive T cells in response to stimulation by dendritic cells pulsed with the polypeptides having the amino acid sequences represented by SEQ ID NOs: 3 to 23, respectively. Lane 1 shows the result obtained when the above treatment was carried out without adding any polypeptide (Mock); Lane 2 shows the result obtained when the above treatment was carried out with the addition of a negative control polypeptide having the amino acid sequence represented by SEQ ID NO: 46, which is outside the scope of the present invention; Lane 3 shows the result obtained when the above treatment was carried out with the addition of the full-length SCD1 protein consisting of the amino acid sequence represented by SEQ ID NO: 2.

Figure 3:
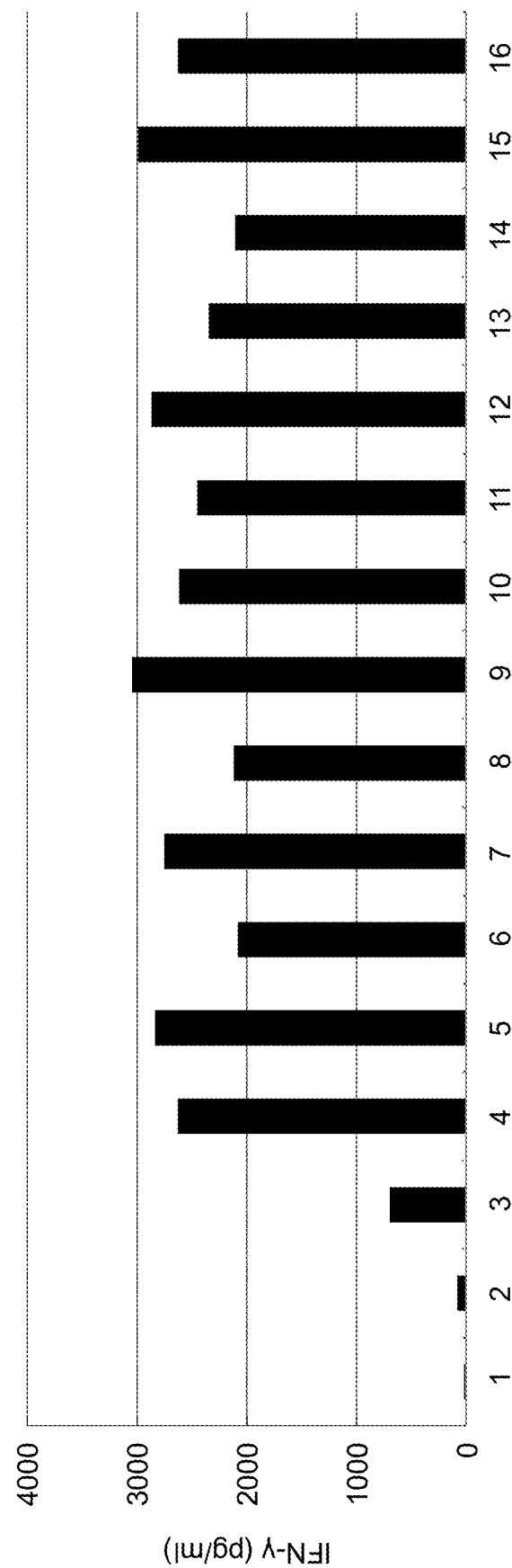

FIG. 3 shows that CD8-positive T cells specific to each of polypeptides consisting of the amino acid sequences represented by SEQ ID NOs: 24 to 36 recognize the complex consisting of the polypeptide and HLA-A24 and produce IFN-γ. In FIG. 3, Lanes 4 to 16 on the horizontal axis show the IFN-γ-producing abilities of HLA-A24-positive CD8-positive T cells in response to stimulation by dendritic cells pulsed with the polypeptides having the amino acid sequences represented by SEQ ID NOs: 24 to 36, respectively. Lane 1 shows the result obtained when the above treatment was carried out without adding any polypeptide (Mock); Lane 2 shows the result obtained when the above treatment was carried out with the addition of a negative control peptide having the amino acid sequence represented by SEQ ID NO: 47, which is outside the scope of the present invention; and Lane 3 shows the result obtained when the above treatment was carried out with the addition of the full-length SCD1 protein consisting of the amino acid sequence represented by SEQ ID NO: 2.

Figure 4A:
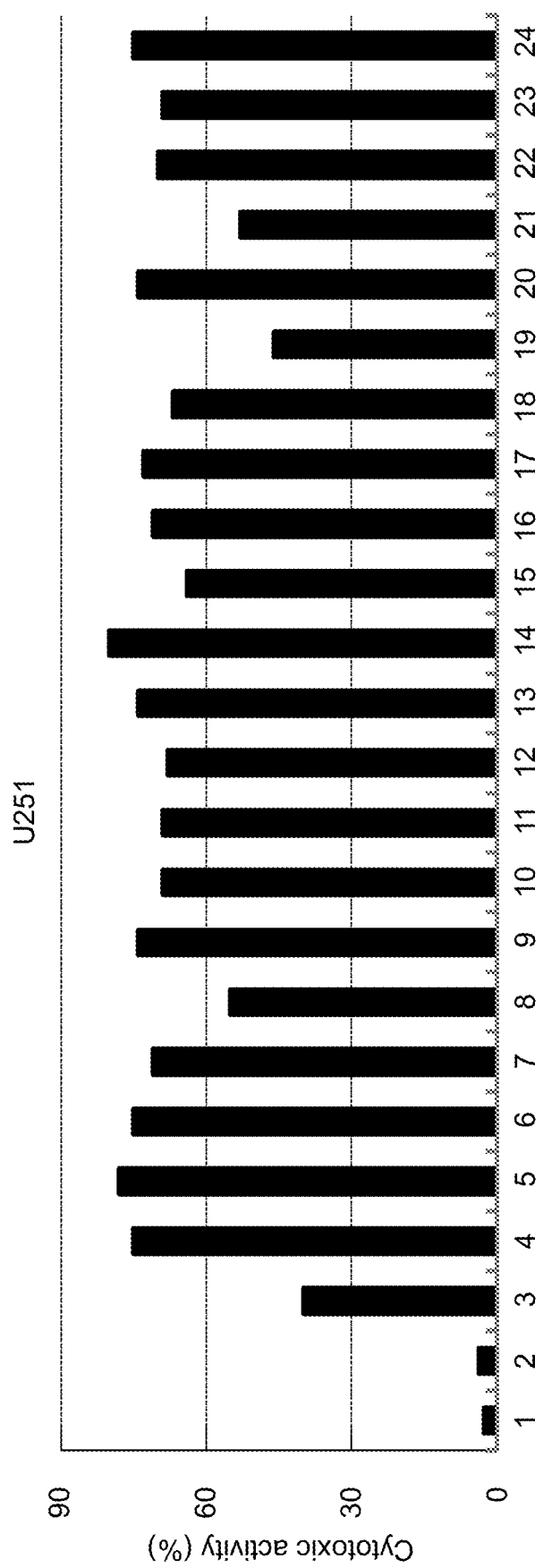

FIG. 4A is a graph showing the cytotoxic activity, against cancer cells, of CD8-positive T cells specific to each of the polypeptides consisting of the amino acid sequences represented by SEQ ID NOs: 3 to 23. In FIG. 4A, Lanes 4 to 24 on the horizontal axis show the cytotoxic activities, against U251 cells, of HLA-A0201-positive CD8-positive T cells induced using the polypeptides having the amino acid sequences represented by SEQ ID NOs: 3 to 23, respectively. Lane 1 shows the cytotoxic activity of CD8-positive T cells (Mock) induced without adding any polypeptide; Lane 2 shows the cytotoxic activity of the CD8-positive T cells induced using the negative control polypeptide (SEQ ID NO: 46); and Lane 3 shows the cytotoxic activity of the CD8-positive T cells induced using the full-length SCD1 protein consisting of the amino acid sequence represented by SEQ ID NO: 2.

Figure 4B:
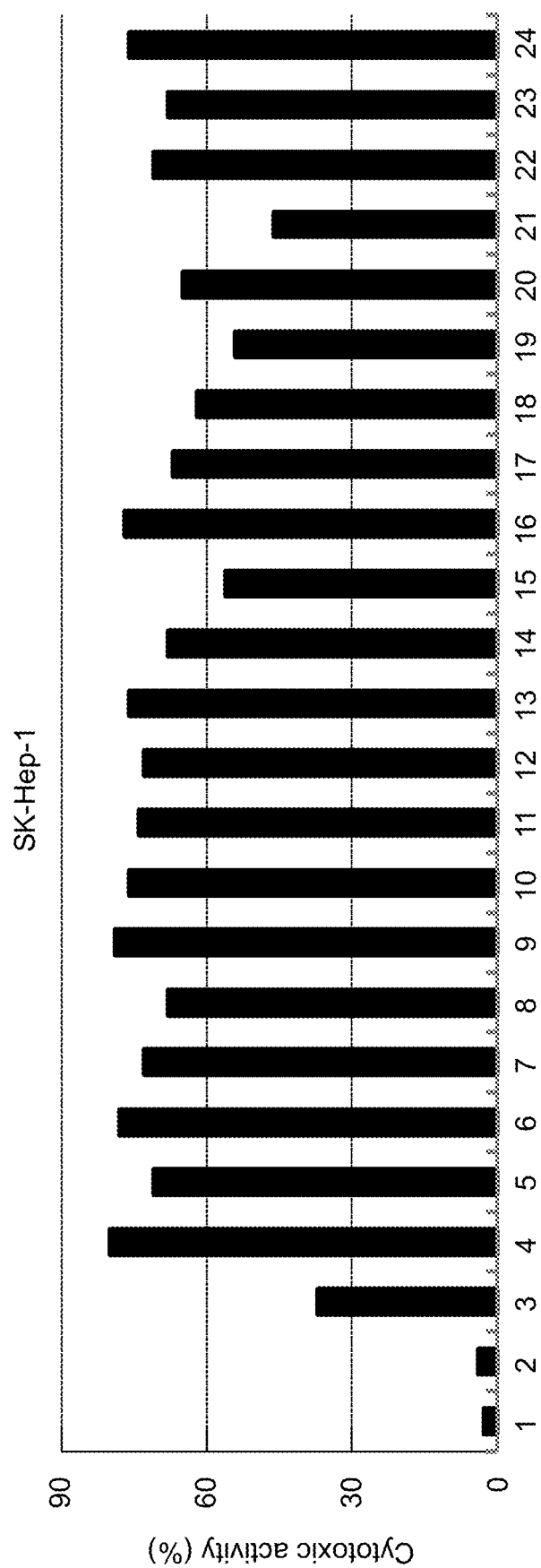

FIG. 4B is a graph showing the cytotoxic activity, against cancer cells, of CD8-positive T cells specific to each of the polypeptides consisting of the amino acid sequences represented by SEQ ID NOs: 3 to 23. In FIG. 4B, Lanes 4 to 24 on the horizontal axis show the cytotoxic activities, against SK-Hep-1 cells, of HLA-A0201-positive CD8-positive T cells induced using the polypeptides having the amino acid sequences represented by SEQ ID NOs: 3 to 23, respectively. Lane 1 shows the cytotoxic activity of CD8-positive T cells (Mock) induced without adding any polypeptide; Lane 2 shows the cytotoxic activity of the CD8-positive T cells induced using the negative control polypeptide (SEQ ID NO: 46); Lane 3 shows the cytotoxic activity of the CD8-positive T cells induced using the full-length SCD1 protein consisting of the amino acid sequence represented by SEQ ID NO: 2.

Figure 5A:
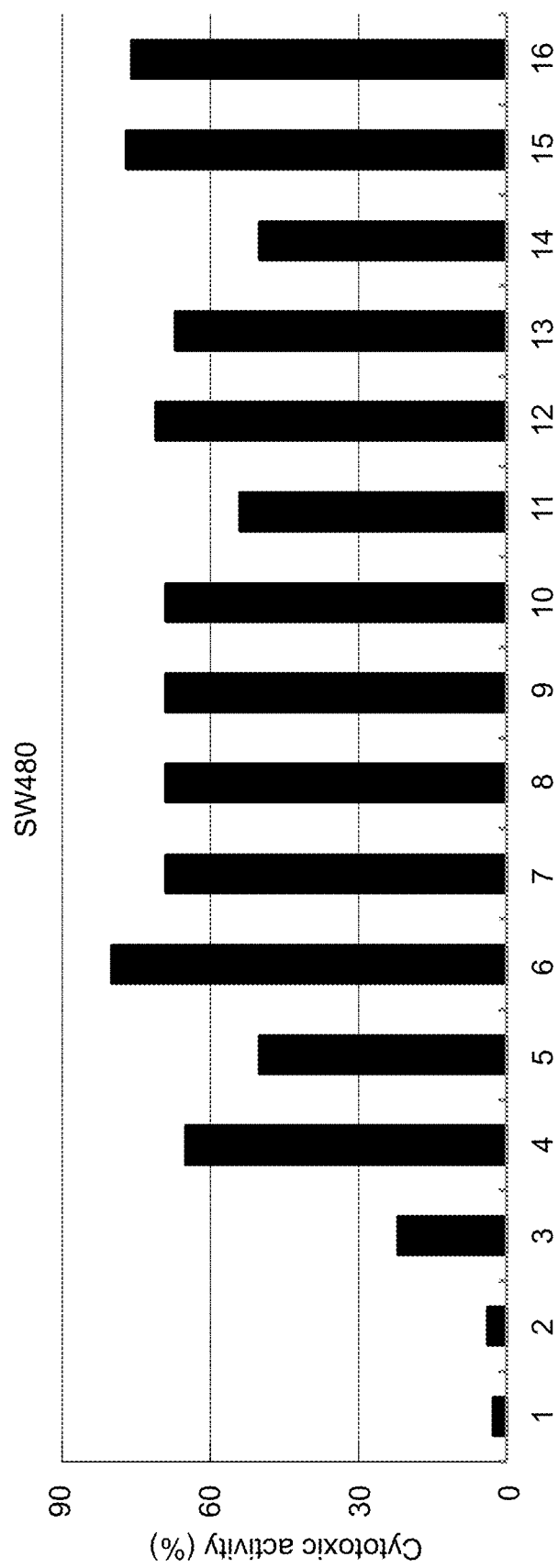

FIG. 5A is a graph showing the cytotoxic activity, against cancer cells, of CD8-positive T cells specific to each of the polypeptides consisting of the amino acid sequences represented by SEQ ID NOs: 24 to 36. In FIG. 5A, Lanes 4 to 16 on the horizontal axis show the cytotoxic activities, against SW480 cells, of HLA-A24-positive CD8-positive T cells stimulated using the polypeptides having the amino acid sequences represented by SEQ ID NOs: 24 to 36, respectively. Lane 1 shows the cytotoxic activity of CD8-positive T cells (Mock) induced without adding any polypeptide; Reference number 2 shows the cytotoxic activity of the CD8-positive T cells induced using the negative control polypeptide (SEQ ID NO: 47); and Lane 3 shows the cytotoxic activity of the CD8-positive T cells induced using the SCD1 protein consisting of the amino acid sequence represented by SEQ ID NO: 2.

Figure 5B:
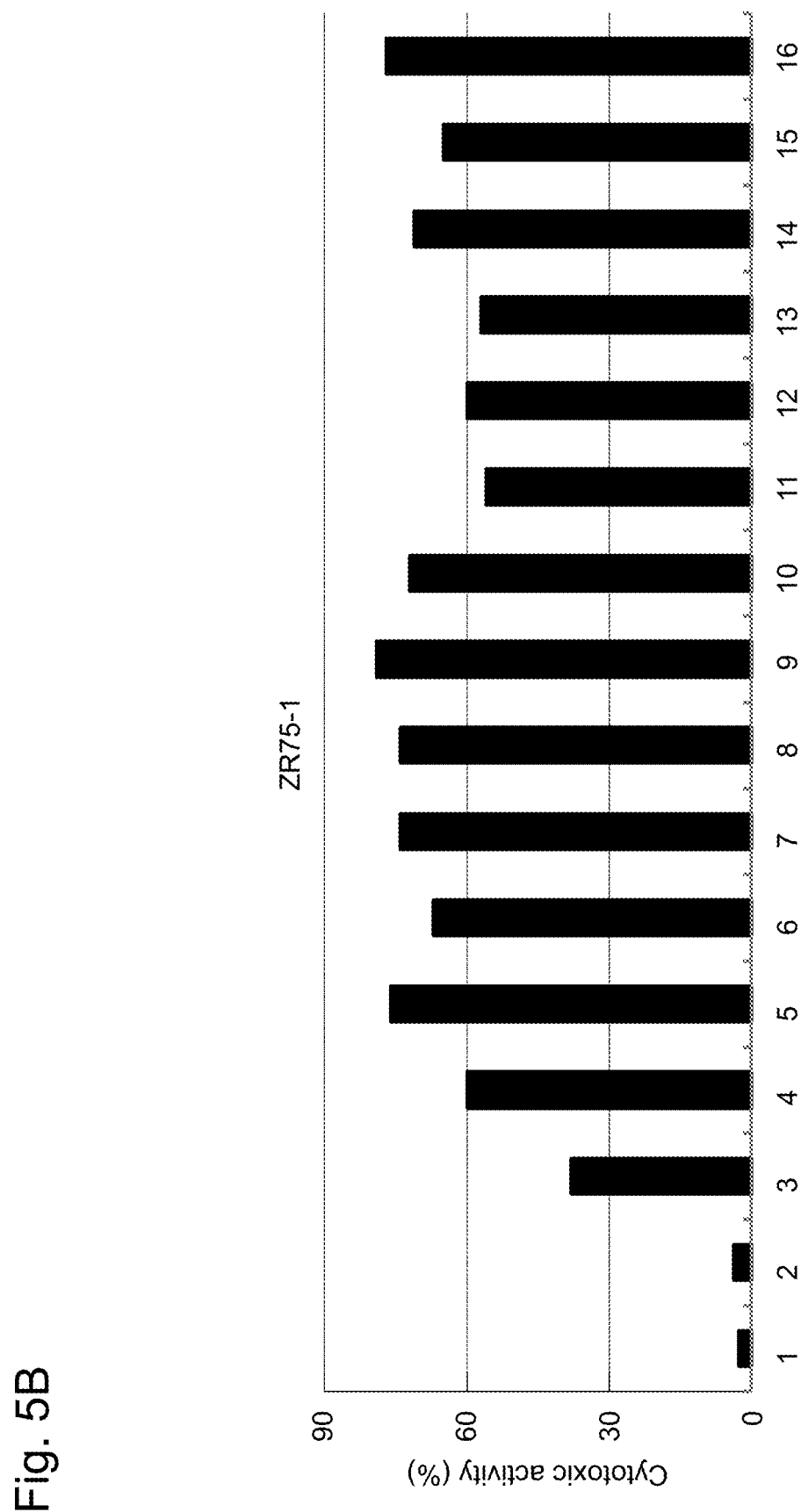

FIG. 5B shows the cytotoxic activity, against cancer cells, of CD8-positive T cells specific to each of the peptides consisting of the amino acid sequences represented by SEQ ID NOs: 24 to 36. Lanes 4 to 16 on the horizontal axis show the cytotoxic activities, against ZR-75-1 cells, of the HLA-A24-positive CD8-positive T cells stimulated using the polypeptides having the amino acid sequences represented by SEQ ID NOs: 24 to 36, respectively. Lane 1 shows the cytotoxic activity of CD8-positive T cells (Mock) induced without adding any polypeptide; Reference number 2 shows the cytotoxic activity of the CD8-positive T cells induced using the negative control polypeptide (SEQ ID NO: 47); and Lane 3 shows the cytotoxic activity of the CD8-positive T cells induced using the SCD1 protein consisting of the amino acid sequence represented by SEQ ID NO: 2.

Figure 6:
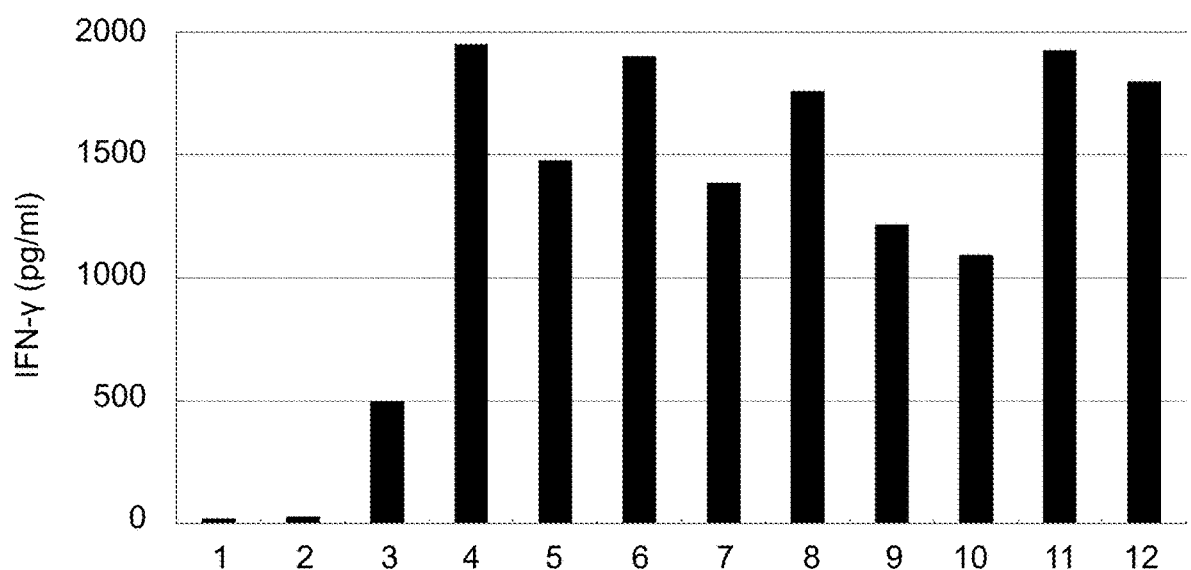

FIG. 6 is a graph showing that CD4-positive T cells specific to each of the polypeptides consisting of the amino acid sequences represented by SEQ ID NOs: 37 to 45 recognize the complex of the polypeptide and HLA-DRB1*04 and produce IFN-γ. In FIG. 6, Lanes 4 to 12 on the horizontal axis show the IFN-γ-producing abilities of HLA-DRB1*04-positive CD4-positive T cells in response to stimulation by dendritic cells pulsed with the polypeptides having the amino acid sequences represented by SEQ ID NOs: 37 to 45, respectively. Lane 1 shows the Mock result obtained when the above treatment was carried out without adding any polypeptide; Lane 2 shows the result obtained when the above treatment was carried out with the addition of a negative control polypeptide having the amino acid sequence represented by SEQ ID NO: 48, which is outside the scope of the present invention; and Lane 3 shows the result obtained when the above treatment was carried out with the addition of the full-length SCD1 protein consisting of the amino acid sequence represented by SEQ ID NO: 2.

DESCRIPTION OF EMBODIMENTS

<Polypeptide>

In the present invention, the term "polypeptide" refers to a molecule formed by peptide bonding of a plurality of amino acids. The polypeptides according to the present invention include not only polypeptide molecules composed of a large number of amino acids but also low-molecular-weight molecules (oligopeptides) composed of a small number of amino acids.

The polypeptide constituting the immune inducer according to the present invention may be, for example, at least one polypeptide having an immune-inducing activity and selected from the group of polypeptides (a) or (b) below:

(a) polypeptides consisting of 7 or more consecutive amino acids within the region of positions 34 to 50 (17 amino acids), positions 69 to 148 (80 amino acids), positions 178 to 195 (18 amino acids), positions 207 to 242 (36 amino acids), positions 247 to 280 (34 amino acids) and positions 296 to 332 (37 amino acids) in the human SCD1 protein consisting of the amino acid sequence represented by SEQ ID NO: 2, when the initiator methionine is defined as position 1;

(b) polypeptides comprising one to several amino acid deletions, substitutions, insertions or additions in the amino acid sequence of any one of the polypeptides (a).

In the present invention, the expression "consisting of an amino acid sequence" means that amino acid residues are arranged in a specific order. Therefore, for example, a "polypeptide consisting of the amino acid sequence represented by SEQ ID NO: 2" refers to a polypeptide which has the amino acid sequence of Met Asp Pro Ala . . . (omitted) . . . Tyr Lys Ser Gly represented by SEQ ID NO: 2, and which has a size of 359 amino acid residues. Further, in the present specification, the "polypeptide consisting of the amino acid sequence represented by SEQ ID NO: 2" is often abbreviated as the "polypeptide of SEQ ID NO: 2", for example. The same applies for the expression "consisting of a base sequence".

The term "immune-inducing activity" as used in the present invention refers to an ability to activate and propagate T cells that respond to cancer cells expressing the SCD1 protein. Specifically, the immune-inducing activity means that: the IFN-γ-producing ability of cytotoxic T cells and/or helper T cells stimulated by the SCD1 protein or a partial polypeptide thereof is higher than that of non-stimulated control T cells; the cytotoxic activity against cancer cells expressing the SCD1 protein of the cytotoxic T cells stimulated by the SCD1 protein or a partial polypeptide thereof is higher than that of the non-stimulated control T cells; the cytotoxic activity of the helper T cells stimulated by the SCD1 protein or a partial polypeptide thereof is enhanced, as compared to that of the non-stimulated control T cells; or the cytotoxic T cells or helper T cells stimulated by the SCD1 protein or a partial polypeptide thereof proliferate more than that of the non-stimulated control T cells.

The proliferation of cells can be confirmed by: visual observation; cell counting under a microscope; flow cytometry; the amount of tritium thymidine in the medium incorporated into the cells; and the like. Further, the measurement of the IFN-γ-producing ability can be performed, for example, by the known ELISPOT assay, and the like. Specifically, as will be described in the Examples below, for example, T cells are first cocultured with a polypeptide whose immune-inducing activity is to be evaluated (the SCD1 protein or a partial polypeptide thereof in the present invention) and antigen-presenting cells derived from peripheral blood mononuclear cells (hereinafter, referred to as "PBMCs"), to allow T cells to be contacted with the antigen-presenting cells presenting the polypeptide to be evaluated. Subsequently, the amount of IFN-γ produced by the T cells is measured using an antibody specific to IFN-γ. This allows for measuring the number of immune cells in the T cells. The immune-inducing activity can then be evaluated based on the thus obtained measurement results.

The cytotoxic activity can be evaluated, for example, by coculturing T cells with a polypeptide whose cytotoxic activity is to be evaluated (in the present invention, it corresponds to the SCD1 protein or a partial polypeptide thereof) and antigen-presenting cells derived from PBMCs, and then analyzing whether or not the T cells show an ability to suppress the proliferation of tumor cells or to kill tumor cells (hereinafter, referred to as "cytotoxic activity") in vitro. The contact between the T cells and the antigen-presenting cells can be achieved by coculturing both of the cells in a liquid medium, as will be describe later. The measurement of the cytotoxic activity can be carried out, for example, by a known method referred to as the $^{51}$Cr release assay, described in Int. J. Cancer, 58: P 317, 1994.

By administering the T cells induced as described above to a cancer-bearing living body, the size of tumor can be reduced or tumor can be regressed due to the cytotoxic activity of the T cells. Therefore, the above described immune-inducing activity can also be evaluated as an ability to suppress the proliferation of cancer cells, or as an ability to cause a reduction in size or the disappearance of a cancer tissue (tumor) (hereinafter, referred to as "anti-tumor activity").

In cases where the above described polypeptide is used for treatment or prevention of cancer, the evaluation of the immune-inducing activity is preferably carried out using the cytotoxic activity or the anti-tumor activity as an index, although the index is not particularly limited thereto.

Since a polypeptide of about 7 or more amino acid residues can include an epitope and such a polypeptide can exhibit antigenicity and immunogenicity, and can have an immune-inducing activity, as is well known in the art, and thus can be used as the immune inducer according to the present invention.

Accordingly, the polypeptide (a) is a polypeptide consisting of 7 or more consecutive amino acids, preferably 8, 9 or 10 or more consecutive amino acids, within the region of positions 34 to 50, positions 69 to 148, positions 178 to 195, positions 207 to 242, positions 247 to 280 and positions 296 to 332 in the amino acid sequence represented by SEQ ID NO: 2; and having an immune-inducing activity. The polypeptide particularly preferably has the amino acid sequence of positions 34 to 50, positions 69 to 148, positions 178 to 195, positions 207 to 242, positions 247 to 280, positions 296 to 332 in the amino acid sequence represented by SEQ ID NO: 2;

As a principle of immune induction by administration of a cancer antigen polypeptide, the polypeptide is incorporated into an antigen-presenting cell and then degraded into smaller fragments by peptidases in the cell, and subsequently, the fragments of the antigenic peptide are presented on the surface of the antigen-presenting cell. It is known that cytotoxic T cells and the like recognize antigens presented on the cell surface, and selectively kill cancer cells presenting the antigens on the cell surface. Further, it is also known that helper T cells recognize antigens presented on the surface of antigen-presenting cells, and enhance the induction of cytotoxic T cells that selectively kill cancer cells presenting the antigens on the on the cell surface. The size of the antigen polypeptide presented on the surface of the antigen-presenting cell is relatively small, and is about 7 to 30 amino acids. Therefore, in terms of allowing the polypeptide to be presented on antigen-presenting cells, the polypeptide (a) is preferably of about 7 to 30 consecutive amino acids, in the amino acid sequence of positions 34 to 50, positions 69 to 148, positions 178 to 195, positions 207 to 242, positions 247 to 280, positions 296 to 332 in the amino acid sequence represented by SEQ ID NO: 2. It is sufficient that the polypeptide consists of about 8 to 30, about 9 to 30 or about 9 to 25 amino acids. These relatively small polypeptides may be presented directly on the surface of the antigen-presenting cells without being incorporated into the cells.

Further, since the polypeptide incorporated into an antigen-presenting cell is cleaved at random sites by peptidases in the cell to yield various polypeptide fragments, and the resulting polypeptide fragments are then presented on the surface of the antigen-presenting cell, the administration of a large polypeptide, such as one having the amino acid sequence of positions 34 to 50, positions 69 to 148, positions 178 to 195, positions 207 to 242, positions 247 to 280, positions 296 to 332 in the amino acid sequence represented by SEQ ID NO: 2, inevitably leads to the production of polypeptide fragments active for immune induction via antigen-presenting cells, due to the degradation of the polypeptide in the antigen-presenting cells. Therefore, a large polypeptide can also be used for immunity induction via antigen-presenting cells. For example, the polypeptide may consist of 30 or more amino acids, preferably 40 or more, more preferably 50 or more, and still more preferably 100 or more amino acids.

Further, the polypeptides according to the present invention can be obtained by being checked with a checking medium, such as HLA Peptide Binding Predictions (http://bimas.dcrtnih.gov/molbio/hla_bind/index.html) in Bioinformatics & Molecular Analysis Selection (BIMAS), or SYFPEITHI, which can search epitope peptides consisting of from 8 to 25, preferably from 9 to 24, and more preferably from 9 to 23 amino acids and having binding motifs for class I molecules or class II molecules of MHC (HLA, in humans) to be described later, to carry out the screening of peptides which may be epitope peptides. Specifically, the polypeptide according to the present invention is a polypeptide consisting of 7 or more consecutive amino acids within the region of positions 34 to 50, positions 69 to 148, positions 178 to 195, positions 207 to 242, positions 247 to 280 and positions 296 to 332 in the amino acid sequence represented by SEQ ID NO: 2. Examples of the polypeptide according to the present invention include: polypeptides represented by SEQ ID NOs: 3 to 45; and polypeptides each comprising as a partial sequence any one of the polypeptides consisting of the amino acid sequences represented by SEQ ID NOs: 3 to 45, and having 10 to 30 amino acid residues. Among the polypeptides represented by SEQ ID NOs: 3 to 45, and the polypeptides each comprising as a partial sequence any one of the polypeptides consisting of the amino acid sequences represented by SEQ ID NOs: 3 to 45 and having 10 to 30 amino acid residues, the immune-inducing activity of the polypeptides represented by SEQ ID NOs: 3 to 36 is due to the binding to MHC class I molecules, and the immune-inducing activity of the polypeptides represented by SEQ ID NOs: 37 to 45 is due to the binding to MHC class II molecules.

On the other hand, the polypeptide (b) is a polypeptide comprising one or several amino acid substitutions, deletions, insertions or additions in the amino acid sequence of the polypeptide (a), and which has an immune-inducing activity. For example, the polypeptides according to the present invention include a polypeptide comprising one or several amino acid substitutions, deletions, insertions or additions in the amino acid sequence represented by any one of SEQ ID NOs: 3 to 45.

The term "several" as used in the present invention refers to an integer of from 2 to 10, preferably an integer of from 2 to 6, more preferably an integer of 2 to 4, and still more preferably an integer of 2 or 3.

In general, it is thought that the modification of one or several amino acids in a polypeptide does not affect the functions of the original polypeptide; in some cases, such a modification is thought to even enhance a desired function of the original polypeptide. In fact, a modified peptide comprising one to several modifications (namely, substituted, deleted, added and/or inserted) in the amino acid sequence of the original amino acid sequence is known to retain the biological activity of the original peptide (Mark et al., 1984, Proc Natl Acad Sci USA, 81: 5662-5666, Zoller and Smith, 1982, Nucleic Acids Res. 10: 6487-6500, Dalbadie-McFarland et al., 1982, Proc Natl Acad Sci USA. 79: 6409-6413). Accordingly, the polypeptide (b) also may exhibit an immune-inducing activity, and thus may be used for the preparation of the immune inducer according to the present invention.

The 20 types of amino acids constituting naturally-occurring proteins can be classified into groups of amino acids with similar properties, such as, for example: neutral amino acids with side chains having low polarity (Gly, Ile, Val, Leu, Ala, Met and Pro); neutral amino acids having hydrophilic side chains (Asn, Gln, Thr, Ser, Tyr and Cys); acidic amino acids (Asp and Glu), basic amino acids (Arg, Lys and His); and aromatic amino acids (Phe, Tyr and Trp). It is known, in many cases, that the substitutions of amino acids within the same group do not alter the properties of the polypeptide. Therefore, in cases where an amino acid residue(s) in the polypeptide (a) of the present invention is/are substituted, the substitution(s) is/are preferably carried out within the same group, because it increases the likelihood of retaining the immune-inducing activity.

Further, the polypeptide (b) may be a polypeptide which has a sequence identity of 90% or more, preferably 95% or more, more preferably 98% or more, and still more preferably 99% or more or 99.5% or more to the polypeptide consisting of 7 or more consecutive amino acids within the region of positions 34 to 50, positions 69 to 148, positions 178 to 195, positions 207 to 242, positions 247 to 280, positions 296 to 332 in the amino acid sequence represented by SEQ ID NO: 2, for example, to any of the polypeptides consisting of the amino acid sequences represented by SEQ ID NOs: 3 to 45, and which has an immune-inducing activity.

As used herein, the term "sequence identity" between amino acid sequences (or base sequences) refers to a percent value obtained by: aligning two amino acid sequences (or base sequences) to be compared such that the number of matched amino acid residues (or bases) between the amino acid sequences (or base sequences) is maximized; and dividing the number of matched amino acid residues (or the number of matched bases) by the total number of amino acid residues (or the total number of bases). When aligning sequences, a gap(s) is/are inserted into one or both of the two sequences to be compared, if required. Such alignment of sequences can be carried out using a known program such as BLAST, FASTA or CLUSTAL W. In cases where a gap(s) is/are inserted, the above-described total number of amino acid residues is the number of residues obtained by counting one gap as one amino acid residue. When the thus counted total number of amino acid residues is different between the two sequences to be compared, the sequence identity (%) is calculated by dividing the number of matched amino acid residues by the total number of amino acid residues in the longer sequence.

When used in connection with treatment or prevention of cancer, the polypeptide according to the present invention should be expressed on the surface of a cell or an exosome, preferably as a complex of the peptide and any of various classes of HLA. Accordingly, for the polypeptides according to the present invention, it is preferred to select a peptide having not only an immune-inducing activity, but also a high binding affinity to various classes of HLA. For this purpose, the peptide may be modified by substitution, insertion, deletion and/or addition of its amino acid residue(s), to obtain a modified peptide having an improved binding affinity. Since the regularity of the sequences of the peptides presented via binding to various classes of HLA is known, in addition to the regularity of naturally presented peptides (J Immunol, 1994, 152: 3913; Immunogenetics, 1995, 41: 178; J Immunol, 1994, 155: 4307), it is possible to introduce a modification based on such a regularity into the immunogenic peptide according to the present invention. For example, the substitution of the second amino acid from the N terminus with leucine or methionine, and/or the substitution of the amino acid at the C terminus with valine or leucine may be desirable for the purpose of improving the binding affinity to HLA-A24. Accordingly, a peptide having the amino acid sequence of any one of SEQ ID NOs: 24 to 36, in which the second amino acid from the N terminus is substituted with leucine or methionine, and/or the amino acid at the C terminus is substituted with valine or leucine, is also within the scope of the present invention.

Substitutions can be introduced not only at the terminal amino acids, but also at potential TCR recognition site(s) of peptides. Several studies have demonstrated that an amino acid-substituted peptide has the same or a superior immune-inducing activity as compared to the original peptide, and examples of the amino acid-substituted peptide include CAP1, p53 (264-272), Her-2/neu (369-377) and gp100 (209-217) (Zaremba et al. 1997, Cancer Res. 57: 4570-4577, T. K. Hoffmann et al. 2002, J Immunol. 168 (3): 1338-47, S. O. Dionne et al. 2003, Cancer Immunol immunother. 52: 199-206, and S. O. Dionne et al.2004, Cancer Immunology, Immunotherapy, 53: 307-314).

In addition to the above described modifications, it is also possible to link the polypeptide according to the present invention with another substance(s), as long as the resulting linked polypeptide retains the necessary immune-inducing activity of the original peptide. Examples of the other substance include but not limited to peptides, lipids, sugars and sugar chains, acetyl groups, and natural and synthetic polymers. The peptide can also include a modification such as glycosylation, side-chain oxidation or phosphorylation, provided that the biological activity of the original peptide is not impaired due to the modification. These types of modifications can be carried out to confer additional functions (such as targeting function and delivery function) to the polypeptide, or to stabilize the polypeptide. For example, it is known in the art to introduce a D-amino acid, an amino acid mimic or a non-natural amino acid into a polypeptide in order to enhance the in vivo stability thereof; and this concept can be utilized in the polypeptides according to the present invention. The stability of a polypeptide can be assayed by several methods. For example, the stability can be tested using peptidases as well as various types of biological media such as human plasma and serum (see, for example, Verhoef et al., 1986, Eur J Drug Metab Pharmacokin, 11: 291-302).

Further, the polypeptide according to the present invention may be linked to another peptide(s) via a spacer(s) or a linker(s). Examples of the other peptide include but not limited to epitope peptides derived from other polypeptides. Alternatively, two or more polypeptides according to the present invention may be liked via a spacer(s) or a linker(s).

The peptides to be linked via a spacer(s) or a linker(s) may be the same, or different from each other. The types of the spacer and the linker are not particularly limited, and examples thereof include those composed of peptides, more preferably, those composed of peptides having one or more cleavage sites that can be cleaved by enzymes such as peptidases, proteases and proteasomes. The linker or spacer may be, for example, AAY (P. M. Daftarian et al., J Trans Med, 2007, 5:26), AAA, NKRK (R. P. M. Sutmuller et al., J Immunol. 2000, 165: 7308-7315), or one to several lysine residues (S. Ota et al., 2002, Can Res. 62: 1471-1476, K. S. Kawamura et al., 2002, J Immunol. 168: 5709-5715), but not limited thereto. The present invention contemplates a polypeptide linked to another peptide(s) via a spacer(s) or a linker(s).

In cases where the polypeptides according to the present invention contain cysteine residues, these polypeptides tend to form dimers via disulfide bonds between the SH groups of the cysteine residues. Therefore, the dimers of these polypeptides are also included in the polypeptides according to the present invention.

The polypeptides according to the present invention can be prepared using known techniques. For example, the polypeptides can be synthesized by a chemical synthesis method such as the Fmoc method (fluorenylmethyloxycarbonyl method) or the tBoc method (t-butyloxycarbonyl method). Further, they can be synthesized by conventional methods using various types of commercially available peptide synthesizers.

In addition, the polypeptide of interest may be obtained using known genetic engineering techniques, by: preparing a polynucleotide encoding the above polypeptide; incorporating the polynucleotide into an expression vector; introducing the vector into a host cell; and then allowing the polypeptide of interest to be produced in the host cell. When obtaining the polypeptide of interest from the host cells, the polypeptide can be purified or isolated such that the polypeptide does not substantially include other naturally-occurring host cell proteins and fragments thereof, or other arbitrary chemical substances.

The polynucleotide encoding the above polypeptide can be easily prepared by a known genetic engineering technique or a conventional method using a commercially available nucleic acid synthesizer. For example, DNA having the base sequence of SEQ ID NO: 1 can be prepared by carrying out PCR using a human chromosomal DNA or cDNA library as a template, and a pair of primers designed to amplify the base sequence represented by SEQ ID NO: 1. The reaction conditions for the PCR can be set as appropriate, and examples thereof include but not limited to repeating a cycle consisting of reactions at: 94° C. for 30 seconds (denaturation), 55° C. for 30 seconds to 1 minute (annealing) and 72° C. for 2 minutes (extension), for 30cycles, followed by a reaction at 72° C. for 1 minute. Further, the desired DNA can be isolated by preparing an appropriate probe(s) or primer(s) based on the information of the base sequence represented by SEQ ID NO: 1 and the amino acid sequence, and screening a cDNA library of human or the like using the probe(s) or primer(s). The cDNA library is preferably prepared from a cell, organ or tissue expressing the protein of SEQ ID NO: 2. The above described operations such as preparation of a probe(s) or primer(s), construction of a cDNA library, screening of a cDNA library and cloning of a gene of interest are known to those skilled in the art, and can be carried out according to the methods described, for example, in in Green, M. R. and Sambrook, J., 2012, Molecular Cloning: A Laboratory Manual Fourth Ed., Cold Spring Harbor Laboratory Press, Cold Spring Harbor, N.Y.; Current Protocolin Molecular Biology: www.currentprotocols.com; and the like. From the thus obtained DNA, DNA encoding the polypeptide (a) can be obtained. Further, since the codons encoding each amino acid are known, the base sequence of a polynucleotide encoding a specific amino acid sequence can be easily specified. Accordingly, the base sequence of a polynucleotide encoding the above described polypeptide (b) can also be easily specified, and thus, such a polynucleotide can also be synthesized using a commercially available nucleic acid synthesizer according to a conventional method.

The host cell may be any cell as long as it can express the above described polypeptide. Examples of prokaryotic cells include but not limited to *E. coli;* and Examples of eukaryotic cells include but not limited to mammalian cultured cells including monkey kidney cells COS-1 and Chinese hamster ovary cells CHO; budding yeast; fission yeast; silkworm cells; and *Xenopus laevis* egg cells.

In cases where a prokaryotic cell is used as the host cell, an expression vector containing an origin that enables its replication in a prokaryotic cell, a promoter, a ribosome binding site, a DNA cloning site a terminator etc. is used. Examples of the expression vector for *E. coli* include the pUC system, pBluescript II, pET expression system and pGEX expression system. The polypeptide encoded by the DNA can be expressed in the prokaryotic host cell by incorporating a DNA encoding the above polypeptide into such an expression vector, transforming a prokaryotic host cell with such a vector, and then culturing the resulting transformant. In this process, the polypeptide can also be expressed as a fusion protein with another protein.

In cases where a eukaryotic cell is used as the host cell, an expression vector for eukaryotic cells containing a promoter, a splicing site, poly(A) addition site, etc. is used. Examples of such an expression vector include pKA1, pCDM8, pSVK3, pMSG, pSVL, pBK-CMV, pBK-RSV, EBV vector, pRS, pcDNA3, pMSG and pYES2. In the same manner as described above, the polypeptide encoded by the DNA can be expressed in the eukaryotic host cell by incorporating a DNA encoding the above polypeptide into such an expression vector, transforming a eukaryotic host cell with such a vector, and then culturing the resulting transformant. In cases where pINDN5-His, pFLAG-CMV-2, pEGFP-N1, pEGFP-C1 or the like is used as the expression vector, the above polypeptide can be expressed as a fusion protein to which any of various types of tags, such as His tag, FLAG tag, myc tag, HA tag and GFP, is added.

The introduction of the expression vector into the host cell can be carried out by a known method such as electroporation, the calcium phosphate method, the liposome method or the DEAE dextran method.

The polypeptide of interest can be isolated and purified from the host cells by a combination of known separation operations. Examples of the known separation operations include but not limited to: treatment with a denaturant such as urea or with a surfactant; ultrasonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method also include, as mentioned above, those in the form of a fusion protein with another arbitrary protein. Examples thereof include fusion proteins with glutathione S-transferase (GST) and fusion proteins with a His tag. Accordingly, such a polypeptide in the form of a fusion protein is also included within the scope of the present invention. Further, a polypeptide expressed in the transformed cell may be modified post-translationally in various ways. Such a post-translationally modified polypeptide is also included within the scope of the present invention, as long as it has an immune-inducing activity. Examples of such a post-translational modification include: elimination of N-terminal methionine; N-terminal acetylation; glycosylation; limited degradation by an intracellular protease; myristoylation; isoprenylation and phosphorylation.

<Immune Inducer>

An already existing tumor can be regressed by administering the polypeptide having an immune-inducing activity according to the present invention, or an expression vector containing the gene encoding the polypeptide, to a cancer-bearing living body. Further, the occurrence of a tumor can be prevented by administering the above described polypeptide having an immune-inducing activity or the gene encoding the polypeptide to a living body before the onset of cancer. Accordingly, the polypeptide according to the present invention or the gene encoding the polypeptide may be used as an active ingredient in immune inducer.

The terms "tumor" and "cancer" are each used herein to refer to a malignant neoplasia, and are used interchangeably. In this case, the cancer to be treated is preferably a cancer expressing the SCD1 protein, and more preferably malignant lymphoma, breast cancer, liver cancer, prostate cancer, ovarian cancer, renal cancer, colorectal cancer, stomach cancer, malignant brain tumor, esophageal cancer or lung cancer.

The subject animal is preferably a mammal, more preferably a mammal such as a primate, a pet animal, a domestic animal or a sport animal, still more preferably a human, a dog or a cat, and particularly preferably a human.

The cancer-affected individual (a cancer patient, in cases where the individual is a human) to be treated is preferably a cancer-affected individual whose cancer cells express the SCD1 protein in vivo. Specifically, preferred is a cancer-affected individual screened by the method of detecting cancer described in WO 2011/027807. In particular, the cancer-affected individual is preferably one screened by the fact that the expression levels of antibodies against the SCD1 protein contained in the sample obtained from the subject living body are higher as compared to the expression levels of the antibodies contained the sample obtained from a healthy individual. Examples of the sample to be used for screening of cancer-affected individuals to be treated include body fluids such as blood, serum, plasma, ascites and pleural effusion; tissues; and cells. In cases where the screening is carried out by measuring the expression levels of antibodies against the SCD1 protein, the sample is preferably serum, plasma, ascites or pleural effusion.

The administration of the immune inducer according to the present invention may be carried out either orally or parenterally. However, preferred administration routes are parenteral administrations such as intramuscular administration, subcutaneous administration, intravenous administration and intraarterial administration. In cases where the immune inducer is used for treatment of cancer, it can be administered to a regional lymph node in the vicinity of the tumor to be treated, in order to enhance its anti-cancer activity. The immune inducer can be administered in any dosage amount effective for inducing immunity. For example, in cases where the immune inducer is used for treatment or prevention of cancer, the agent may be administered in an amount effective for treatment or prevention of cancer. The amount effective for treatment or prevention of cancer can be selected as appropriate depending on the size of the tumor, symptoms, body weight and volume of the subject animal, and the like. In cases where the subject animal is a human, the effective amount is usually from 0.0001 to 1,000 µg, and preferably from 0.001 to 1,000 µg per day. The above described dosage amount can be administered in a single dose, or in several divided doses. It is preferred that the above dosage amount be divided and administered several times per day, and that the administration thereof be carried out every several days or several months. As will be specifically described in the Examples below, the immune inducer according to the present invention can regress an already formed tumor. Thus, since the immune inducer can exert its anti-cancer activity also against a small number of cancer cells in the early stages, the development or recurrence of cancer can be prevented by using the agent before the onset or after the treatment of the cancer. In other words, the immune inducer according to the present invention is useful in both the treatment and prevention of cancer, and can be used as an active ingredient in an agent for treating or preventing cancer.

The immune inducer according to the present invention contains as an active ingredient the above described polypeptide according to the present invention, and may consist of a single polypeptide, or of a combination of a plurality of polypeptides. By combining a plurality of the polypeptides according to the present invention, the immunity-inducing activity (activity to induce and activate cytotoxic T cells) of each of the polypeptides is enhanced, and a more efficient treatment or prevention of cancer may be achieved.

The immune inducer according to the present invention can also be used in combination with a known peptide(s) capable of inducing cytotoxic T cells. By combining the polypeptide(s) according to the present invention with such a known peptide(s), the immunity-inducing activity (activity to induce and activate cytotoxic T cells) of each of the polypeptides is enhanced, and a more efficient treatment or prevention of cancer may be achieved. The term "combination" as used in this case includes the case in which the immune inducer according to the present invention and a known peptide(s) capable of inducing cytotoxic T cells are administered separately or simultaneously. The expression "to be administered separately" as used herein means that the immune inducer according to the present invention and a known peptide(s) capable of inducing cytotoxic T cells are administered separately at different time points with a certain time interval therebetween. The order of administration is not limited. On the other hand, the expression "to be administered simultaneously" means that the immune inducer according to the present invention and a known peptide(s) capable of inducing cytotoxic T cells are mixed in advance and administered in the form of a mixture, or that the immune inducer according to the present invention and a known peptide(s) capable of inducing cytotoxic T cells are administered in separate forms but at the same time without any time interval.

The immune inducer according to the present invention can be used in combination with another immune enhancer capable of enhancing the immune response in vivo. The other immune enhancer may be included in the immune inducer according to the present invention, or may be administered to a patient as a separate composition, in combination with the administration of the immune inducer according to the present invention.

The "other immune enhancer" includes, for example, an adjuvant. An adjuvant can enhance the immune response by providing an antigen reservoir (extracellularly or within macrophages), activate macrophages and stimulate specific lymphocytes, so as to enhance the anti-cancer activity. Therefore, in cases where the immune inducer according to the present invention is used as an active ingredient in an agent for treating or preventing cancer, it is preferred that the immune inducer further contain an adjuvant, in addition to the polypeptide according to the present invention as an active ingredient. Many types of adjuvants are known in the art, and any of these adjuvants can be used. Specific examples of the adjuvants include MPL (SmithKline Beecham), analogs of *Salmonella minnesota* Re 595 lipopolysaccharide obtained after purification and acid hydrolysis of the lipopolysaccharide; QS21 (SmithKline Beecham), pure QA-21 saponin purified from an extract of *Quillja saponaria;* DQS21 described in PCT application WO 96/33739 (SmithKline Beecham); QS-7, QS-17, QS-18 and QS-L1 (So, H. S., et al., "Molecules and cells", 1997, 7: 178-186); Freund's incomplete adjuvant; Freund's complete adjuvant; vitamin E; Montanide; alum; CpG oligonucleotides (see, for example, Kreig, A. M., et al., 1995, Nature 374: 546-549); poly-I:C and derivatives thereof (such as poly ICLC); and various water-in-oil emulsions prepared from biodegradable oils such as squalene and/or tocopherol. Among these, Freund's incomplete adjuvant; Montanide; poly-I:C and derivatives thereof; and CpG oligonucleotides are preferred. The mixing ratio of the above-described adjuvant to the polypeptide is typically from about 1:10 to 10:1, preferably from about 1:5 to 5:1, and more preferably about 1:1. However, the adjuvant is not limited to the above-described examples, and any adjuvant known in the art other than those described above can also be used, when administering the immune inducer according to the present invention (see, for example, Goding, "Monoclonal Antibodies: Principles and Practice", 2nd edition, 1986). Methods for preparing a mixture or an emulsion of an immune inducer and an adjuvant are well-known to those skilled in the art of vaccination.

Further, in addition to the above-described adjuvants, factors that stimulate the immune response of the subject may be used as the other immune enhancer. For example, any of various types of cytokines having a property to stimulate lymphocytes and/or antigen-presenting cells can be used as the immune enhancer in combination with the immune inducer according to the present invention. A number of such cytokines capable of enhancing the immune response are known to those skilled in the art, and examples thereof include but not limited to interleukin-12 (IL-12), GM-CSF, IL-18, interferon-α (IFN-α), interferon-β (IFN-β), interferon-ω (IFN-ω), interferon-γ (IFN-γ), and Flt3 ligand, which have been shown to enhance the protective action of vaccines. Any of such factors can also be used as the above-described immune enhancer, and can be administered to a patient in combination with the immune inducer according to the present invention, either by being incorporated into the immune inducer according to the present invention, or as a separate composition.

<Agent for Treating or Preventing Cancer>

The immune inducer according to the present invention can be used as an active ingredient in an agent for treating or preventing cancer.

The agent for treating or preventing cancer can be formulated by mixing, as appropriate, the immune inducer according to the present invention with an additive(s) such as a pharmaceutically acceptable carrier, diluent and/or excipient suitable for each dosage form.

Formulation methods and additives which can be used are well-known in the art of pharmaceutical formulation, and any of the methods and additives can be used. Specific examples of the additives include but not limited to: diluents such as physiological buffer solutions; excipients such as sugar, lactose, corn starch, calcium phosphate, sorbitol and glycine; binders such as syrup, gelatin, gum arabic, sorbitol, polyvinyl chloride and tragacanth; and lubricants such as magnesium stearate, polyethylene glycol, talc and silica. Examples of the dosage form include oral preparations such as tablets, capsules, granules, powders and syrups; and parenteral preparations such as inhalants, injection solutions, suppositories and solutions. These formulations can be prepared by commonly known production methods.

<Antigen-Presenting Cells>

The polypeptide can be presented by the antigen-presenting cells by bringing the above described polypeptide into contact with antigen-presenting cells in vitro. In other words, the above described polypeptide (a) or (b) can be used as an agent for treating antigen-presenting cells. As the antigen-presenting cells, dendritic cells or B cells having MHC class I molecules and class II molecules can be preferably used. A variety of MHC class I molecules and class II molecules have been identified and are well known. MHC molecules in humans are referred to as HLA. Examples of HLA class I molecules include HLA-A, HLA-B and HLA-C; and more specific examples thereof include HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401 and HLA-Cw0602. Examples of HLA class II molecules include HLA-DR, HLA-DQ and HLA-DP; and more specific examples thereof include HLA-DRB1*01, HLA-DRB1*03, HLA-DRB1*04, HLA-DRB1*0405, HLA-DRB1*07, HLA-DRB1*08, HLA-DRB1*11, HLA-DRB1*13, HLA-DRB1*15, HLA-DRB1*15, HLA-DQA1, HLA-DQB1 and HLA-DPB1.

The dendritic cells or B cells having MHC class I or MHC class II molecules can be prepared from blood or the like by a well-known method. For example, tumor specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-related peptide to the culture system.

An immune response desirable for treating cancer may be induced by administering an effective amount of the thus obtained dendritic cells. The cells to be used can be obtained from bone marrow or umbilical cord blood provided by a healthy individual, or bone marrow or peripheral blood or the like of the patient himself. The use of autologous cells obtained from the patient himself is preferred, because they are highly safe and serious side effects are expected to be avoided. The peripheral blood or bone marrow may be any of a fresh sample, a cold-stored sample and a frozen sample. The peripheral blood may be obtained by culturing whole blood, or by culturing separated leukocyte components alone, and the latter is more efficient and thus preferred. Further, mononuclear cells may be separated among the leukocyte components. In cases where the cells to be used are those derived from bone marrow or umbilical cord blood, all the cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are derived, as well as CD4-positive cells and the like. There is no particular limitation on the method for producing the cytokines to be used, and any cytokine, either natural or recombinant, can be used as long as its safety and physiological activity have been confirmed. It is preferred to use a preparation with assured quality for medical use, in a minimum amount necessary. The concentration of the cytokine(s) to be added is not particularly limited as long as it can induce dendritic cells. In general, the total concentration of the cytokine(s) is preferably from about 10 to 1,000 ng/mL, and more preferably from about 20 to 500 ng/mL. The culture can be carried out using a well-known medium commonly used for culturing leukocytes. The temperature for cultivation is not particularly limited as long as it can propagate the leukocytes; however, a temperature of about 37° C., which is the human body temperature, is most preferred. Further, the atmospheric environment during the culture is not particularly limited as long as it can propagate the leukocytes; however, it is preferred that 5% $CO_2$ is allowed to flow. The period of time for cultivation is not particularly limited as long as a required number of cells can be induced within the period. The culture is usually carried out for a period of from 3 days to 2 weeks. The apparatuses used for separation and culture of the cells can be selected as appropriate. Preferred are apparatuses whose safety for medical use has been confirmed, and which can be operated stably and simply. As for the cell culturing apparatus, in particular, it is possible to use, not only a common vessel such as a Petri dish, flask or bottle, but also a multi-layer vessel, a multi-stage vessel, a roller bottle, a spinner bottle, a bag-type culture vessel, a hollow fiber column or the like.

The process for bringing the above-described polypeptide into contact with the antigen-presenting cells in vitro can be carried out by a well-known method. For example, it can be achieved by culturing the antigen-presenting cells in a culture medium containing the above described polypeptide. The concentration of the peptide in the medium is not particularly limited, and it is usually from about 1 to 100 μg/mL, and preferably from about 5 to 20 μg/mL. The cell density during the culture is not particularly limited, and it is usually from about $10^3$ to $10^7$ cells/mL, and preferably from about $5 \times 10^4$ to $5 \times 10^6$ cells/mL. The culture is preferably carried out at 37° C. under an atmosphere of 5% $CO_2$, according to a conventional method. The maximum length of the peptide which can be presented on the surface of the antigen-presenting cells is usually a length of about 30 amino acid residues. Therefore, in cases where the antigen-presenting cells are brought into contact with the polypeptide in vitro, the polypeptide may be prepared such that its length is not more than about 30 amino acid residues, but not particularly limited thereto.

By culturing the antigen-presenting cells with the above described polypeptide, the peptide is incorporated into MHC molecules of the antigen-presenting cells, and presented on the surface of the antigen-presenting cells. Thus, isolated antigen-presenting cells containing the complex of the polypeptide and the MHC molecule may be prepared using the above described polypeptide. Such antigen-presenting cells can present the polypeptide to T cells in vivo or in vitro, induce cytotoxic T cells or helper T cells specific to the polypeptide, and propagate these cells.

By bringing the thus prepared antigen-presenting cells containing the complex of the above described polypeptide and the MHC molecule, into contact with T cells, in vitro, it is possible to induce cytotoxic T cells or helper T cells specific to the polypeptide, and to allow the proliferation of these cells. This can be achieved by coculturing the antigen-presenting cells and T cells in a liquid medium. For example, it can be carried out by suspending the antigen-presenting cells in a liquid medium, placing the resulting suspension in a vessel, such as in wells of a microplate, adding T cells thereto, and then culturing the cells. The mixing ratio of the antigen-presenting cells to the T cells when coculturing these cells is not particularly limited, and is usually from about 1:1 to 1:100, and preferably from about 1:5 to 1:20 in terms of the number of the cells. The density of the antigen-presenting cells to be suspended in the liquid medium is not particularly limited, and it is usually from about 100 to 10 million cells/ml, and preferably from about 10,000 to 1 million cells/ml. Coculture is preferably carried out at 37° C. under an atmosphere of 5% $CO_2$, according to a conventional method. The period of time for culturing is not particularly limited, and it is usually from about 2 days to 3 weeks, and preferably from about 4 days to 2 weeks. Further, coculture is preferably carried out in the presence of one or more types of interleukins such as IL-2, IL-6, IL-7 and/or IL-12. In such cases, the concentration of IL-2 or IL-7 is usually from about 5 to 20 U/mL, the concentration of IL-6 is usually from about 500 to 2000 U/mL, and the concentration of IL-12 is usually from about 5 to 20 ng/mL, but not limited thereto. The above described coculture may be repeated once or several times, adding fresh antigen-presenting cells. For example, the operation of discarding the culture supernatant after the coculture and adding a fresh suspension of the antigen-presenting cells to further carrying out the coculture, may be repeated once or several times. The conditions for each coculture may be the same as described above.

The above described coculture allows for the induction and proliferation of cytotoxic T cells and helper T cells specific to the polypeptide. Thus, isolated T cells which selectively bind to the complex of the polypeptide and the MHC molecule may be prepared with the use of the above described polypeptide.

As will be described in the Examples below, the gene (SCD1 gene) encoding the SCD1 protein is expressed specifically in each of: malignant lymphoma tissues, malignant lymphoma cells, breast cancer tissues, breast cancer cells, liver cancer tissues, liver cancer cells, prostate cancer tissues, prostate cancer cells, ovarian cancer tissues, ovarian cancer cells, renal cancer tissues, renal cancer cells, colorectal cancer tissues, colorectal cancer cells, stomach cancer tissues, stomach cancer cells, malignant brain tumor tissues, malignant brain tumor cells, esophageal cancer tissues, esophageal cancer cells, lung cancer tissues, and lung cancer cells. Therefore, a significantly higher amount of the SCD1 protein is thought to be present in the cells of these cancer types, than in normal cells. When cytotoxic T cells or helper T cells prepared as described above are administered to a living body, while a part of the SCD1 protein present in cancer cells is presented by MHC molecules on the surface of the cancer cells, the thus presented protein serves as a marker to allow the cytotoxic T cells to damage the cancer cells, or enhance the cytotoxic activity of the cytotoxic T cells. Since antigen-presenting cells presenting the above described polypeptide can induce, and propagate cytotoxic T cells and helper T cells specific to the polypeptide, also in vivo, the administration of the antigen-presenting cells to a living body can also allow the cytotoxic T cells to damage the cancer cells, or enhance the cytotoxic activity of the cytotoxic T cells. In other words, the cytotoxic T cells and helper T cells as well as the antigen-presenting cells prepared using the above polypeptide are also useful as agents for treating or preventing cancer, as is the immune inducer according to the present invention.

In the case of administering the above described isolated antigen-presenting cells or isolated T cells to a living body, these cells are preferably prepared by treating antigen-presenting cells or T cells collected from the patient to be treated, with the polypeptide (a) or (b) as described above, in order to avoid the immune response in the living body, that attacks these cells as foreign substances.

The agent for treating or preventing cancer comprising as an active ingredient the antigen-presenting cells or isolated T cells is preferably administered via a parenteral administration route such as intravenous or intraarterial administration. The dosage amount is selected as appropriate depending on the symptoms, the purpose of administration and the like. The dosage amount is usually from one to 10 trillion cells, and preferably from 1 million to 1 billion cells, which amount is preferably administered once in several days or several months. The formulation may be, for example a suspension of the cells in physiological buffered saline, and the formulation may be used in combination with another anti-cancer agent(s), cytokine(s) and/or the like. Further, one, or two or more additives known in the field of pharmaceutical formulation can also be added to the formulation.

<Gene Vaccine>

Immune induction, namely, the induction of antibody production or cytotoxic T cells in the body of a subject animal, can also be achieved by allowing a polynucleotide encoding the polypeptide (a) or (b) to be expressed in the living body. This provides an effect equivalent to that provided by administering the polypeptide. In other words, the immune inducer according to the present invention may comprise as an active ingredient a recombinant vector which contains the polynucleotide encoding the above described polypeptide (a) or (b) and which can express the polypeptide in a living body. Such a recombinant vector capable of expressing an antigen polypeptide, which will be shown in the Examples below, is also referred to as a "gene vaccine".

The vector to be used for the production of a gene vaccine is not particularly limited as long as it can express a polypeptide in a cell of the subject animal (preferably, in a mammalian cell). The vector may be either a plasmid vector or a virus vector, and any vector known in the field of gene vaccines may be used. The polynucleotide, such as DNA or RNA, encoding the above described polypeptide can be easily prepared as described above, by a conventional method. Further, the polynucleotide may be incorporated into a vector using a method well-known to those skilled in the art.

The gene vaccine is preferably administered by a parenteral administration route, such as intramuscular, subcutaneous, intravenous or intraarterial administration. The dosage amount of the gene vaccine can be selected as appropriate depending on the type of the antigen and the like, and it is usually from about 0.1 µg to 100 mg, and preferably from about 1 µg to 10 mg, in terms of the weight of the gene vaccine per 1 kg of body weight.

The method utilizing a virus vector may be, for example, a method in which a polynucleotide encoding the above described polypeptide is incorporated into an RNA virus or DNA virus, such as a retrovirus, adenovirus, adeno-associated virus, herpes virus, vaccinia virus, pox virus, poliovirus or Sindbis virus, and then a subject animal is infected with the resulting virus. In particular, a method utilizing a retrovirus, adenovirus, adeno-associated virus, vaccinia virus or the like is particularly preferred.

Examples of other methods include a method in which an expression plasmid is directly administered intramuscularly (DNA vaccine method), the liposome method, lipofectin method, microinjection method, calcium phosphate method and electroporation method. Of these, the DNA vaccine method and liposome method are particularly preferred.

Methods for allowing the gene encoding the polypeptide used in the present invention to actually act as a pharmaceutical include: an in vivo method comprising directly introducing the gene into the body of a subject; and an ex vivo method comprising collecting a certain type of cells from a subject animal, and introducing the gene into the cells ex vivo, followed by returning the cells to the body of the subject animal. Of these, the in vivo method is more preferred.

In cases where the gene is administered by the in vivo method, the gene may be administered through an appropriate administration route depending on the disease to be treated, symptoms and the like. For example, the gene can be administered by an intravenous, intraarterial, subcutaneous, intramuscular administration or the like. In the case of administering the gene by the in vivo method, the gene may be formulated into a dosage form such as a solution; but generally formulated as an injection solution or the like containing DNA encoding the above described peptide according to the present invention as an active ingredient. A commonly used carrier(s) may be added thereto if required. In the case of using a liposome or membrane fusion liposome (Sendai virus (HVJ)-liposome or the like) containing the DNA, the liposome may be formulated into a liposome preparation such as a suspension, frozen preparation or centrifugally concentrated frozen preparation.

In the present invention, "the base sequence represented by SEQ ID NO:1" includes not only the base sequence actually represented by SEQ ID NO: 1, but also the sequence complementary thereto. Thus, "a polynucleotide having the base sequence represented by SEQ ID NO:1" includes a single-stranded polynucleotide having the base sequence actually represented by SEQ ID NO:1, a single-stranded polynucleotide having the base sequence complementary thereto, and a double-stranded polynucleotide consisting of these single-stranded polynucleotides. When the polynucleotide encoding the polypeptide used in the present invention is prepared, any one of these base sequences is to be selected as appropriate, which selection can be easily carried out by those skilled in the art.

EXAMPLES

The present invention will be more specifically described below, by way of Examples.

Example 1

Analysis of Expression in Various Tissues (1) Analysis of SCD1 Gene Expression in Various Cancer Cell Lines The gene sequence (SEQ ID NO: 1) encoding the amino acid sequence of human SCD1 protein is obtained from Gene Bank. The expression of the thus obtained gene in various types of human cell lines was analyzed by RT-PCR (Reverse Transcription-PCR). The reverse transcription reaction was carried out as follows. Specifically, from 50 to 100 mg of each tissue or 5 to 10×10$^6$ cells of each cell line, total RNA was extracted using TRIZOL reagent (manufactured by Life Technologies, Inc.) according to the protocol described in the attached instructions. The thus obtained total RNA was used to synthesize cDNA, using Superscript First-Strand Synthesis System for RT-PCR (manufactured by Life Technologies, Inc.) according to the protocol described in the attached instructions. As the cDNAs of normal human tissues (brain, hippocampus, testis, colon and placenta), Gene Pool cDNA (manufactured by Life Technologies, Inc.), QUICK-Clone cDNA (manufactured by Clontech Laboratories, Inc.) and Large-Insert cDNA Library (manufactured by Clontech Laboratories, Inc.) were used. The PCR reaction was carried out as follows, using primers specific to the obtained gene (the base sequences of the primes are represented by SEQ ID NOs: 49 and 50). Specifically, reagents and an attached buffer were added to prepare a mixture having a total volume of 25 µL, and containing 0.25 µL of a sample prepared by the reverse transcription reaction, 2 µM each of the above described primers, 0.2 mM each of dNTPs, and 0.65 U of ExTaq polymerase (manufactured by Takara Shuzo Co., Ltd.). The reaction was then carried out using Thermal Cycler (manufactured by Bio-Rad laboratories Inc.) by repeating a cycle consisting of reactions at 94° C. for 30 seconds, 55° C. for 30 seconds and 72° C. for 1 minute, for 30 times. At the same time, primers specific to GAPDH, which is a housekeeping gene (the base sequences of human GAPDH primers are represented by SEQ ID NOs: 51 and 52) were used as a control for comparison.

Figure 1:
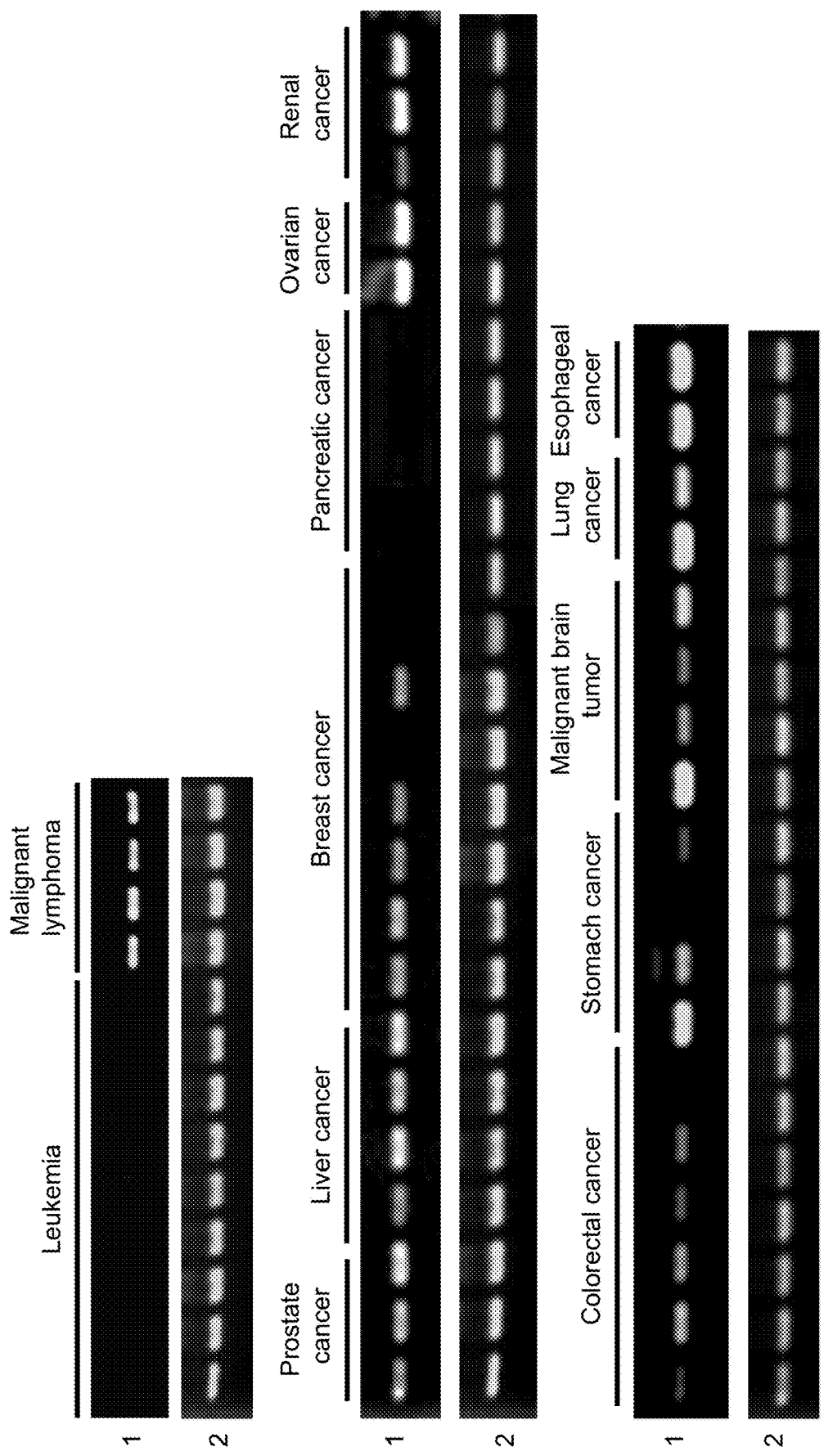
FIG. 1 shows the expression patterns of SCD1 gene, in human tumor tissues and cancer cell lines. Reference number 1 indicates the expression pattern of the human SCD1 gene. Reference number 2 indicates the expression pattern of human GAPDH gene, which is a human housekeeping gene.

As a result, as shown in FIG. 1, the expression of the human SCD1 gene was detected in most of the cancer cell lines, namely, in the cell lines of malignant lymphoma, breast cancer, liver cancer, prostate cancer, ovarian cancer, renal cancer, colorectal cancer, stomach cancer, malignant brain tumor, esophageal cancer and lung cancer.

(2) Expression of SCD1 Protein in Human Cancer Tissue (Immunohistochemical Staining)

Immunohistochemical staining was carried out on 72 cancer tissue specimens in a paraffin-embedded multiple cancer tissue array (manufactured by Biomax Inc.). The human cancer tissue array was treated at 60° C. for 3 hours, and placed in a staining jar filled with xylene, and the operation of replacing xylene with a fresh one every 5 minutes was repeated 3 times. Subsequently, the same operation was carried out using ethanol and PBS-T instead of xylene. The human cancer tissue array was placed in a staining jar filled with a 10 mM citrate buffer solution (pH 6.0) containing 0.05% Tween 20, treated at 125° C. for 5 minutes, and then left to stand at room temperature for 40 minutes or more. Excess moisture around the tissue sections was wiped off with Kimwipes, the tissue sections were encircled using a DAKOPEN, and an adequate amount of Peroxidase Block (manufactured by DAKO) was added dropwise thereto. After allowing the array to stand at room temperature for 5 minutes, the array was placed in a staining jar filled with PBS-T, and the operation of replacing PBS-T with a fresh one every 5 minutes was repeated 3 times. A PBS-T solution containing 10% FBS, as a blocking solution, was applied to the array, and the array was left to stand in a moist chamber at room temperature for 1 hour. Subsequently, a commercially available rabbit polyclonal antibody (manufactured by Sigma-Aldrich Co. LLC.) which reacts to the SCD1 protein was diluted with a PBS-T solution containing 5% FBS to a concentration of 10 µg/mL, and the resulting solution was applied to the array, followed by allowing the array to stand overnight in a moist chamber controlled at 4° C. After washing the array with PBS-T for 10 minutes, for 3 times, an adequate amount of Peroxidase Labelled Polymer Conjugated (manufactured by DAKO)

was added dropwise thereto, and the array was left to stand in a moist chamber at room temperature for 30 minutes. After washing the array with PBS-T for 10 minutes, for 3 times, a DAB color-developing solution (manufactured by DAKO) was applied thereto, and the array was left to stand at room temperature for about 10 minutes. Thereafter, the color-developing solution was discarded, and the array was washed with PBS-T for 10 minutes, for 3 times, followed by rinsing with distilled water. The array was then successively dipped in 70%, 80%, 90%, 95% and 100% ethanol solutions for 1 minute each, and then left to stand overnight immersed in xylene. The glass slide of the array was recovered, mounted with Glycergel Mounting Medium (manufactured by DAKO), and then observed.

As a result, strong expression of SCD1 protein was observed in most of the tissues of the cancers tested, namely: malignant lymphoma, breast cancer, liver cancer, prostate cancer, ovarian cancer, renal cancer, colorectal cancer, stomach cancer, malignant brain tumor, esophageal cancer and lung cancer.

Example 2

Induction of Peptide Epitope-Reactive CD8-Positive T Cells (1) Prediction of Peptide Motifs which Bind to HLA-A0201 and HLA-A24

Information on the amino acid sequence of the human SCD1 protein represented by SEQ ID NO: 2 was obtained from GenBank. For the prediction of HLA-A0201 and HLA-A24 binding motifs, the amino acid sequence of the human SCD1 protein was analyzed with a computer-based prediction program using a known BIMAS software (available at http://bimas.dcrt.nih.gov/molbio/hla_bind/). As a result, 21 types of polypeptides consisting of the amino acid sequences represented by SEQ ID NOs: 3 to 23, which were expected to be capable of binding to the HLA-A0201 molecule; and 13 types of polypeptides consisting of the amino acid sequences represented by SEQ ID NOs: 24 to 36, which were expected to be capable of binding to the HLA-A24 molecule; were selected. All the selected polypeptides were synthesized by Greiner Japan Co. Ltd. that provides custom peptide synthesis services. The quality of the synthesized polypeptides has been guaranteed by HPLC analysis and mass spectrometry.

(2) Induction of Peptide Epitope-Reactive CD8-Positive T Cells

Peripheral blood was separated from the blood of an HLA-A0201-positive healthy individual. The peripheral blood was layered on Lymphocyte separation medium (OrganonpTeknika Corporation, Durham, N.C.), and then centrifuged at 1,500 rpm at room temperature for 20 minutes. A PBMC-containing fraction was collected and washed 3 times (or more) with a cold phosphate buffer solution to obtain PBMCs. The thus obtained PBMCs were suspended in 20 mL of AIM-V medium (manufactured by Life Technologies, Inc.), and allowed to adhere to a culture flask (manufactured by Falcon Plastics Co.) for 2 hours under the conditions of 37° C. and 5% $CO_2$. Non-adherent cells were used for the preparation of T cells, and adherent cells were used for preparing dendritic cells.

The adherent cells were cultured in AIM-V medium in the presence of IL-4 (1,000 U/ml) and GM-CSF (1,000 U/ml). Six days later, the medium was replaced with AIM-V medium supplemented with IL-4 (1,000 U/mL), GM-CSF (1,000 U/mL), IL-6 (1,000 U/mL, manufactured by Genzyme Corporation), IL-1β (10 ng/mL, manufactured by Genzyme Corporation) and TNF-α (10 ng/mL, manufactured by Genzyme Corporation), and the cells were cultured for another 2 days. The resulting population of the non-adherent cells was used as the dendritic cells.

The thus prepared dendritic cells were suspended in AIM-V medium at a cell density of $1\times10^6$ cells/mL. Each of the peptides which were selected in the above described (1) and expected to be capable of binding to the HLA-A0201 molecule was added to the cells at a concentration of 10 μg/mL, followed by culturing for 4 hours under the conditions of 37° C. and 5% $CO_2$, using a 96-well plate. After the cultivation, the cells were irradiated with X-ray (3000 rad), washed with AIM-V medium, suspended in AIM-V medium containing 10% human AB serum (manufactured by Nabi Biopharmaceuticals Inc.), IL-6 (1,000 U/mL) and IL-12 (10 ng/mL, manufactured by Genzyme Corporation), and then placed in wells of a 24-well plate at a population of $1\times10^5$ cells per well. Further, the prepared T cell population was added to the wells at a population of $1\times10^6$ cells per well, and the cells were cultured under the conditions of 37° C. and 5% $CO_2$. Then, seven days later, dendritic cells obtained in the same manner as described above by the treatment with each peptide and the subsequent X-ray irradiation were suspended (cell density: $1\times10^5$ cells/mL) in AIM-V medium containing 10% human AB serum (manufactured by Nabi Biopharmaceuticals Inc.), IL-7 (10 U/mL, manufactured by Genzyme Corporation) and IL-2 (10 U/mL, manufactured by Genzyme Corporation), and the resulting suspension was added to the wells of the 24-well plate at a population of $1\times10^5$ cells per well, followed by further culturing the cells. The same procedures were repeated 4 times at intervals of 7 days, and the stimulated T cells were then collected. Thereafter, the induction of CD8-positive T cells was confirmed by flow cytometry.

Further, the same treatment as described above was carried out, using as a negative control, a peptide (SEQ ID NO: 46) having a sequence outside the scope of the present invention; and using as Comparative Examples, the SCD1 protein which had been prepared according to Example 3 in WO 2012/157736 and which consists of the amino acid sequence represented by SEQ ID NO: 2.

The induction of peptide epitope-reactive CD8-positive T cells was attempted also for the peptides expected to be capable of binding to the HLA-A24 molecule, in the same manner as described above, using dendritic cells and a T cell population induced from peripheral blood of an HLA-A24-positive healthy individual. Further, the same treatment as described above was carried out, using as a negative control, a peptide (SEQ ID NO: 47) having a sequence outside the scope of the present invention; and using as a Comparative Example, the SCD1 protein consisting of the amino acid sequence represented by SEQ ID NO: 2.

Example 3

Determination of Cytotoxic T Cell Antigen Epitopes (1) IFN-γ-Producing Ability

In order to examine the specificity of the respective T cells induced in Example 2 (2), to the respective epitope peptides and the protein, dendritic cells expressing the HLA-A0201 molecule were pulsed with various types of polypeptides. The dendritic cells were prepared by culturing in AIM-V medium supplemented with each polypeptide at a concentration of 10 μg/mL under the conditions of 37° C. and 5%

CO$_2$ for 4 hours. As the various types of polypeptides, the respective polypeptides represented by the amino acid sequences of SEQ ID NOs: 3 to 23 and expected to be capable of binding to the HLA-A0201 molecule, the negative control polypeptide (SEQ ID NO: 46) and the SCD1 protein consisting of the amino acid sequence represented by SEQ ID NO: 2 were used. To 5×10$^4$ dendritic cells which had been pulsed with each peptide, 5×10$^3$ T cells were added, and the cells were cultured for 24 hours in AIM-V medium containing 10% human AB serum, in a 96-well plate. Each supernatant after the cultivation was collected, and the amount of produced IFN-γ was measured by ELISA.

As a result, a clearly higher IFN-γ production was observed in the supernatants of Lanes 4 to 24 in which the dendritic cells pulsed with the polypeptides having the amino acid sequences represented by SEQ ID NOs: 3 to 23 were used, as compared to the supernatants of Lanes 1 and 2 in which the dendritic cells not pulsed with any polypeptide and the dendritic cells pulsed with the negative control polypeptide, respectively, were used (FIG. 2). These results revealed that the peptides of SEQ ID NOs: 3 to 23 are T cell epitope peptides having an ability to specifically stimulate the proliferation of HLA-A0201-positive CD8-positive T cells, and to induce IFN-γ production. Further, it has also been revealed that the amounts of IFN-γ produced by T cells stimulated with these peptides were markedly higher than the amounts of IFN-γ produced by T cells stimulated with the full-length SCD1 protein (Lane 3) consisting of the amino acid sequence represented by SEQ ID NO: 2. In other words, these results indicate that the polypeptides of SEQ ID NOs: 3 to 23 have a markedly higher immune-inducing activity. In addition, although the sequences of SEQ ID NOs: 3 to 23 having the above described immune-inducing activity are included in the amino acid sequence of the full-length SCD1 protein represented by SEQ ID NO: 2, the amount of IFN-γ produced by the T cells stimulated with the full-length SCD1 protein of SEQ ID NO: 2 was low. The reason for this is thought to be that the full-length SCD1 protein failed to demonstrate sufficient immune-inducing activity, because the amino acid sequence of the full-length SCD1 protein also includes a number of sequences which inhibit the immune-inducing activity.

Further, in order to examine the specificity of each of the peptide epitope-reactive CD8-positive T cells induced in Example 3 (2) using the polypeptides having the amino acid sequences represented by SEQ ID NOs: 24 to 36, to peptide epitopes, the amount of IFN-γ produced by the T cells, against dendritic cells expressing the HLA-A24 molecule, which dendritic cells had been pulsed with each of: the polypeptides of SEQ ID NOs: 24 to 36 (Lanes 4 to 16); the negative control polypeptide having the amino acid sequence represented by SEQ ID NO: 47; and the full-length SCD1 protein having the amino acid sequence represented by SEQ ID NO: 2; was measured by ELISA, in the same manner as described above.

As a result, a markedly higher IFN-γ production was observed in the culture supernatants of Lanes 4 to 16 in which the dendritic cells pulsed with the polypeptides of SEQ ID NOs: 24 to 36 were used, as compared to the supernatants of Lanes 1 and 2 in which the dendritic cells not pulsed with any polypeptide and the dendritic cells pulsed with the negative control polypeptide, respectively, were used (FIG. 3).

These results revealed that the polypeptides of SEQ ID NOs: 24 to 36 are T cell epitope peptides having an ability to specifically stimulate the proliferation of HLA-A24-positive CD8-positive T cells, and to induce IFN-γ production. Further, it has also been revealed that that the amounts of IFN-γ produced by T cells stimulated with these polypeptides were markedly higher than the amounts of IFN-γ produced by T cells stimulated with the full-length SCD1 protein having the amino acid sequence represented by SEQ ID NO: 2. The reason for this is thought to be that the full-length SCD1 protein failed to demonstrate sufficient immunity-inducing activity, due to the same reason as described above.

(2) Cytotoxicity Assay

Subsequently, the following were examined: whether or not the polypeptides having the amino acid sequences represented by SEQ ID NOs: 3 to 23, which are used in the present invention, are presented on the HLA-A0201 molecules on tumor cells which are HLA-A0201-positive and which express human SCD1 protein; whether or not the CD8-positive T cells stimulated with the polypeptides according to the present invention can damage the tumor cells which are HLA-A0201-positive and which express the human SCD1 protein; and further, whether or not the above described CD8-positive T cells have a markedly higher ability to damage the tumor cells as compared to the CD8-positive T cells stimulated with the SCD1 protein.

Each of the cell lines whose expression of human SCD1 protein has been confirmed, namely: a human glioma (malignant brain tumor) cell line U251 cells; a leukemia cell line THP1 cells; a liver cancer cell line SK-Hep-1; a breast cancer cell line MCF7; an ovarian cancer cell line OVCAR3; a renal cancer cell line A498; a colorectal cancer cell line HCT116; a stomach cancer cell line AGS; and a lung cancer cell line NCI-H522 (purchased from JCRB, RIKEN and ATCC); were collected into a 50 mL centrifugal tube, in an amount of 10$^6$ cells each. After adding 100 μCi of chromium 51 thereto, the cells were incubated at 37° C. for 2 hours. Thereafter, each type of the cells was washed 3 times with RPMI medium (manufactured by Gibco Brl Co.) containing 10% fetal bovine serum (hereinafter, referred to as FBS; manufactured by Gibco Brl Co.) and placed in wells of a 96-well V-bottom plate at a population of 10$^3$ cells per well. To each well, 5×10$^4$ cells of HLA-A0201-positive CD8-positive T cells suspended in RPMI medium containing 10% FBS, which cells had been induced by stimulation with each of: the polypeptides having the amino acid sequences represented by SEQ ID NOs: 3 to 23, the negative control polypeptides (SEQ ID NO: 46) and the full-length SCD1 protein having the amino acid sequence represented by SEQ ID NO: 2; were further added, followed by culturing for 4 hours under the conditions of 37° C. and 5% CO$_2$. After the cultivation, the amount of chromium 51 released from the damaged tumor cells into each culture supernatant was measured, whereby the cytotoxic activity of the CD8-positive T cells induced by stimulation with each of the polypeptides and the protein was calculated.

As a result, it has been revealed that the HLA-A0201-positive CD8-positive T cells induced by stimulation with the polypeptides having the amino acid sequences represented by SEQ ID NOs: 3 to 23 exhibit a markedly high cytotoxic activity against all of the above described cells. As representative examples, the cytotoxic activity against the U251 cells and the SK-Hep-1 cells are shown in FIG. 4A and FIG. 4B, respectively. It can be seen that the CD8-positive T cells stimulated by the polypeptides having the amino acid sequences represented by SEQ ID NOs: 3 to 23 (Lanes 4 to 24, respectively) exhibit a markedly higher cytotoxic activity against the U251 cells and the SK-Hep-1 cells, as compared to the CD8-positive T cells (Lane 3) stimulated by the full-length SCD1 protein. On the other hand, the CD8-positive T cells induced with the negative control polypeptide (Lane 2) did not show any cytotoxic activity, the result being roughly the same as the case of Mock (Lane 1). These results suggest that each of the polypeptides of SEQ ID NOs: 3 to 23 used in the present invention is presented on the HLA-A0201 molecules on tumor cells which are HLA-A0201-positive and which express human SCD1 polypeptide, and in addition, that the polypeptides according to the present invention have an ability to induce CD8-positive cytotoxic T cells capable of damaging such tumor cells. Further, regardless of the fact that the amino acid sequence of the full-length SCD1 protein includes the sequences of SEQ ID NOs: 3 to 23, the CD8-positive T cells stimulated with the full-length SCD1 protein exhibited a markedly lower cytotoxic activity, as compared to that of the CD8-positive T cells stimulated with the polypeptides having the amino acid sequences of SEQ ID NOs: 3 to 23 (Lanes 3, 4 to 24). The reason for this is thought to be that the SCD1 protein failed to induce T cells having a high cytotoxic activity, because the amino acid sequence of the SCD1 protein includes a number of sequences which inhibit the immune-inducing activity.

Similarly, it was examined whether or not the polypeptides of SEQ ID NOs: 24 to 36 are presented on the HLA-A24 molecules on tumor cells which are HLA-A24-positive and which express human SCD1 protein; whether or not the CD8-positive T cells stimulated with the polypeptides according to the present invention can damage the tumor cells which are HLA-A24-positive and which express the human SCD1 protein; and further, whether or not the above described CD8-positive T cells have a markedly higher ability to damage the tumor cells as compared to the CD8-positive T cells stimulated with the SCD1 protein.

Chromium 51 was allowed to be incorporated into cell lines which are HLA-A24-positive and which express human SCD1 protein, namely: a human glioma cell line KNS-42; a liver cancer cell line SK-Hep1; a renal cancer cell line Caki1; a colorectal cancer cell line SW480; a stomach cancer cell line MKN45; a prostate cancer cell line PC3; a breast cancer cell line ZR75-1 (purchased from JCRB, RIKEN and ATCC). Each type of the cells was cultured with the HLA-A24-positive CD8-positive T cells which had been induced by stimulation with each of: the polypeptides having the amino acid sequences represented by SEQ ID NOs: 24 to 36; the negative control polypeptide (SEQ ID NO: 47); and the full-length SCD1 protein, and the amount of chromium 51 released from the damaged cells into each culture supernatant was measured.

As a result, it has been revealed that the HLA-A24-positive CD8-positive T cells stimulated with the polypeptides having the amino acid sequences represented by SEQ ID NOs: 24 to 36 exhibit a markedly high cytotoxic activity, which is well above the generally predictable range, against all types of cancer cells used. As representative examples, the cytotoxic activity against the SW480 cells and the ZR75-1 cells are shown in FIG. 5 A and FIG. 5B, respectively. It can be seen that the CD8-positive T cells stimulated by the polypeptides having the amino acid sequences represented by SEQ ID NOs: 24 to 36 (Lanes 4 to 16, respectively) exhibit a markedly higher cytotoxic activity against the SW480 cells and the ZR75-1 cells, as compared to the CD8-positive T cells (Lane 3) stimulated by the full-length SCD1 protein. On the other hand, the CD8-positive T cells induced with the negative control polypeptide (Lane 2) did not show any cytotoxic activity, the result being roughly the same as the case of Mock (Lane 1). Thus, it can be seen that each of the polypeptides of SEQ ID NOs: 24 to 36 is presented on the HLA-A24 molecules on cells which are HLA-A24-positive and which express human SCD1 protein, and these results suggest that the polypeptides according to the present invention have an ability to induce CD8-positive cytotoxic T cells capable of damaging such cells.

On the other hand, when the above described cancer cells were exposed to the polypeptides represented by the amino acid sequences of SEQ ID NOs: 3 to 36 and the full-length SCD1 protein consisting of the amino acid sequence represented by SEQ ID NO: 2, no cancer cells were killed at all. This confirmed the fact that these polypeptides do not have an activity to directly kill the cancer cells.

The cytotoxic activity was determined as described above, by mixing $5 \times 10^4$ cells of the CD8-positive T cells stimulated and induced with each of the polypeptides used in the present invention and $1 \times 10^3$ cells of each type of the tumor cells into which chromium 51 was incorporated; culturing each mixture of cells for 4 hours; measuring the amount of chromium 51 released into each culture medium after the cultivation; and calculating the cytotoxic activity of the CD8-positive T cells against each type of the tumor cells (referred to as target cells) according to the following formula*.

*Formula: cytotoxic activity (%)=amount of chromium 51 released from target cells upon addition of CD8-positive T cells/amount of chromium 51 released from target cells upon addition of 1 N hydrochloric acid×100.

Example 4

Induction of CD4-Positive T Cells Reactive with Peptide Epitopes Derived from SCD1 Protein-Derived Peptide For predicting CD4-positive T cell antigen epitopes, the amino acid sequence of the human SCD1 protein was analyzed with a computer-based prediction program using the SYFPEITHI algorithm (by Rammensee), and 9 types of peptides represented by SEQ ID NOs: 37 to 45 and expected to be HLA class II-binding peptides were selected. All the selected peptides were synthesized by Greiner Japan Co. Ltd. that provides custom peptide synthesis services.

Peripheral blood was separated from the blood of an HLA-DRB1*04-positive healthy individual. The peripheral blood was layered on Lymphocyte separation medium (manufactured by OrganonpTeknika Corporation), and centrifuged at 1,500 rpm at room temperature for 20 minutes. A PBMC-containing fraction was collected and washed 3 times (or more) with a cold phosphate buffer solution to obtain PBMCs. The thus obtained PBMCs were suspended in 20 mL of AIM-V medium (manufactured by Life Technologies, Inc.), and allowed to adhere to a culture flask (manufactured by Falcon Plastics Co.) for 2 hours under the conditions of 37° C. and 5% $CO_2$. Non-adherent cells were used for the preparation of T cells, and adherent cells were used for preparing dendritic cells.

The adherent cells were cultured in AIM-V medium in the presence of IL-4 (1,000 U/ml) and GM-CSF (1,000 U/ml). Six days later, the medium was replaced with AIM-V medium supplemented with IL-4 (1,000 U/mL), GM-CSF (1,000 U/mL), IL-6 (1,000 U/mL, manufactured by Genzyme Corporation), IL-1β (10 ng/mL, manufactured by Genzyme Corporation) and TNF-α (10 ng/mL, manufactured by Genzyme Corporation), and the cells were cultured for another 2 days. The obtained population of the non-adherent cells was used as the dendritic cells.

The thus prepared dendritic cells were suspended in AIM-V medium at a cell density of $1 \times 10^6$ cells/mL. Each of the polypeptides of SEQ ID NOs: 37 to 45, the negative control polypeptide (SEQ ID NO: 48) and the SCD1 protein consisting of the amino acid sequence represented by SEQ ID NO: 2 was added to the cells at a concentration of 10 mg/mL, followed by culturing for 4 hours under the conditions of 37° C. and 5% $CO_2$, using a 96-well plate. After the cultivation, the cells were irradiated with X-ray (3000 rad), washed with AIM-V medium, suspended in AIM-V medium containing 10% human AB serum (manufactured by Nabi Biopharmaceuticals Inc.), IL-6 (1,000 U/mL) and IL-12 (10 ng/mL, manufactured by Genzyme Corporation), and then placed in wells of a 24-well plate at a population of $1\times10^5$ cells per well. Further, the prepared T cell population was added to the wells at a population of $1\times10^6$ cells per well, and the cells were cultured under the conditions of 37° C. and 5% $CO_2$. Seven days later, each culture supernatant was discarded. Then, dendritic cells treated with each peptide obtained in the same manner as described above or the SCD1 protein followed by X-ray irradiation were suspended in AIM-V medium containing 10% human AB serum (manufactured by Nabi Biopharmaceuticals Inc.) and IL-2 (10 U/mL, manufactured by Genzyme Corporation), and the resulting suspension was added to the wells of the 24-well plate at a population of $1\times10^5$ cells per well, followed by further culturing the cells. The same procedures were repeated 4 times at intervals of 7 days, and the stimulated T cells were then collected. Thereafter, the induction of CD4-positive T cells was confirmed by flow cytometry. As a result, the induced T cells in each well were confirmed to be proliferated.

Example 5

Determination of SCD1 Protein-Derived Helper T Cell Antigen Epitopes which Stimulate HLA-DRB1*04-Positive CD4-Positive T Cells In order to examine the specificity of the respective CD4-positive T cells induced in the above described Example 4 to the respective peptide proteins, the PBMCs expressing HLA-DRB1*04 molecules were pulsed with various types of polypeptides. The PBMCs were prepared by culturing in AIM-V medium supplemented with each polypeptide at a concentration of 10 µg/mL under the conditions of 37° C. and 5% $CO_2$ for 4 hours. As the various types of polypeptides, the respective polypeptides represented by the amino acid sequences of SEQ ID NOs: 37 to 45, the negative control polypeptide (SEQ ID NO: 48) and the full-length SCD1 protein consisting of the amino acid sequence represented by SEQ ID NO: 2 were used. To $5\times10^4$ PBMCs which had been pulsed with each peptide, $5\times10^4$ CD4-positive T cells were added, and the cells were cultured for 24 hours in AIM-V medium containing 10% human AB serum, in a 96-well plate. Each supernatant after the cultivation was collected, and the amount of produced IFN-γ was measured by ELISA.

As a result, an IFN-γ production of 1,000 pg/mL or more was confirmed in the culture supernatants in the wells of PBMCs pulsed with the respective peptides of SEQ ID NOs: 37 to 45. On the other hand, the production of IFN-γ was barely observed in the culture supernatants in the well of PBMCs pulsed with the negative control polypeptide and in the well of the dendritic cells alone (Mock) not pulsed with any polypeptide. Thus, it has been revealed that the polypeptides represented by the amino acid sequences SEQ ID NOs: 37 to 45 are T cell epitope peptides having an ability to specifically stimulate and propagate the HLA-DRB1*04-positive CD4-positive T cells, and to induce the production of IFN-γ. Further, regardless of the fact that the amino acid sequence of the full-length SCD1 protein includes the above described sequences of SEQ ID NOs: 37 to 45 having an immunity-inducing activity, the amount of IFN-γ produced in the culture supernatant in the well of PBMC cells pulsed with the full-length SCD1 protein was extremely low. The reason for this is thought to be that the SCD1 protein failed to demonstrate sufficient immunity-inducing activity, because the amino acid sequence of the SCD1 protein includes a number of sequences which inhibit the immunity-inducing activity.

Subsequently, it was examined whether or not the polypeptides of SEQ ID NOs: 37 to 45 having an ability to stimulate the proliferation of the HLA-DRB1*04-positive T cells are epitopes which are naturally processed from the SCD1 protein within the antigen-presenting cells and presented on HLA-DR. A lysate of HEK293 cells (purchased from ATCC) transiently expressing the SCD1 protein was added to immature dendritic cells to allow the digestion of the protein, and the maturation of the dendritic cells. Then, it was examined whether or not the T cells stimulated with each of the polypeptides of SEQ ID NOs: 37 to 45, the negative control polypeptide and the SCD1 protein are stimulated by the resulting dendritic cells. Peripheral blood was separated from the blood of an HLA-DRB1*04-positive healthy individual. The peripheral blood was layered on Lymphocyte separation medium, and centrifuged at 1,500 rpm at room temperature for 20 minutes. The interphase containing PBMCs was collected and washed 3 times (or more) with a cold phosphate buffer solution to obtain PBMCs. The thus obtained PBMCs were suspended in 20 mL of AIM-V medium, and allowed to adhere to a culture flask (manufactured by Falcon Plastics Co.) for 2 hours under the conditions of 37° C. and 5% $CO_2$. The adherent cells were cultured in AIM-V medium in the presence of IL-4 (1,000 U/mL) and GM-CSF (1,000 U/mL) for 6 days, to obtain immature dendritic cells. The above described lysate was added to $5\times10^5$ immature dendritic cells, followed by culturing in AIM-V medium supplemented with IL-4 (1,000 U/mL), GM-CSF (1,000 U/mL), IL-6 (1,000 U/mL), IL-1β (10 ng/mL) and TNF-α (10 ng/mL) for 2 days. The cultured dendritic cells were irradiated with X-ray (3000 rad), washed with AIM-V medium, suspended in AIM-V medium containing 10% human AB serum, and then placed in wells of a 96-well plate at a population of $3.3\times10^4$ cells per well. To each well, $5\times10^4$ T cells stimulated with each of the polypeptides of SEQ ID NOs: 37 to 45, the negative control polypeptide and the SCD1 protein were added, and the cells were cultured under the conditions of 37° C. and 5% $CO_2$ for 24 hours. Each supernatant after the cultivation was collected, and the amount of produced IFN-γ was measured by ELISA.

As a result, as shown in FIG. 6, it has been found out that the T cells of Lanes 4 to 12 which were stimulated with the polypeptides of SEQ ID NOs: 37 to 45, respectively, produced IFN-γ in response to stimulation by the dendritic cells to which the SCD1 protein was added. On the other hand, the production of IFN-γ was barely observed in the T cells of Lane 2 stimulated with the negative control polypeptide and the T cells of Lane 1 not stimulated with any polypeptide. Thus, it has been revealed that the polypeptides of SEQ ID NOs: 37 to 45 are epitopes which are naturally processed from the SCD1 protein within the antigen-presenting cells and presented on HLA-DR. Further, the production of IFN-γ in the T cells of Lane 3 pulsed with the full-length SCD1 protein was extremely low, also in the present experiment. The reason for this is thought to be that the full-length SCD1 protein failed to demonstrate sufficient immunity-inducing activity, because the amino acid sequence of the full-length SCD1 protein includes a number of sequences which inhibit the immunity-inducing activity.

INDUSTRIAL APPLICABILITY

The immune inducer according to the present invention containing a polypeptide which exhibits an anti-tumor activity against various types of cancers is useful in the treatment or prevention of cancer, or in the detection of cancer.

All publications, patents, and patent applications cited in this specification are incorporated herein by reference in their entirety.

The invention claimed is:

1. An immune inducer composition comprising, as an active ingredient,
   at least one polypeptide having an immune-inducing activity and selected from the group of polypeptides consisting of the amino acid sequence of any one of SEQ ID NOs: 3 to 45; or
   a recombinant vector comprising at least one polynucleotide encoding any one of the polypeptides, and capable of expressing the polypeptide in vivo; and an immune enhancer.

2. The immune inducer according to claim 1, wherein the polypeptide having an immune-inducing activity binds to an MHC class II molecule.

3. A composition comprising, as an active ingredient, one or more selected from the group consisting of (i) to (iii) below:
   (i) a polypeptide consisting of the amino acid sequence of any one of SEQ ID NOs: 3 to 45;
   (ii) a recombinant vector comprising a polynucleotide encoding the polypeptide, and capable of expressing the polypeptide in vivo; and
   (iii) an isolated antigen-presenting cell comprising a complex of the polypeptide with an MHC molecule; and an immune enhancer.

4. The composition of claim 3, wherein the active ingredient is one or more of the isolated antigen-presenting cell comprising the complex of the polypeptide with the MHC molecule.

5. A method of treating cancer, comprising administering to a subject in need thereof, a composition comprising, as an active ingredient, one or more selected from the group consisting of (i) to (iii) below:
   (i) a polypeptide consisting of the amino acid sequence of any one of SEQ ID NOs: 3 to 45;
   (ii) a recombinant vector comprising a polynucleotide encoding the polypeptide, and capable of expressing the polypeptide in vivo; and
   (iii) an isolated antigen-presenting cell comprising a complex of the polypeptide with an MHC molecule;
   wherein the composition is a pharmaceutical composition further comprising a pharmaceutically acceptable carrier.

6. The method according to claim 5, wherein the cancer is a cancer expressing SCD1 protein.

7. The method according to claim 5, wherein the cancer is malignant lymphoma, breast cancer, liver cancer, prostate cancer, ovarian cancer, renal cancer, colorectal cancer, stomach cancer, malignant brain tumor, esophageal cancer or lung cancer.

8. The method of claim 5, wherein the active ingredient is one or more of the isolated antigen-presenting cell comprising the complex of the polypeptide with the MHC molecule.

* * * * *

SEQUENCE LISTING

<160> NUMBER OF SEQ ID NOS: 52

<210> SEQ ID NO 1
<211> LENGTH: 5473
<212> TYPE: DNA
<213> ORGANISM: Homo sapiens
<220> FEATURE:
<221> NAME/KEY: CDS
<222> LOCATION: (491)..(1570)
<223> OTHER INFORMATION:

<400> SEQUENCE: 1

```
ggcaggacga ggtggcacca aattcccttc ggccaatgac gagccggagt ttacagaagc     60
ctcattagca tttccccaga ggcaggggca ggggcagagg ccgggtggtg tggtgtcggt    120
gtcggcagca tccccggcgc cctgctgcgg tcgccgcgac cctcggcctc tgtctcctcc    180
ccctcccgcc cttacctcca cgcgggaccg cccgcgccag tcaactcctc gcactttgcc    240
cctgcttggc agcggataaa aggggctga ggaaataccg acacggtca cccgttgcca     300 gctctagcct ttaaattccc ggctcgggga cctccacgca ccgcggctag cgccgacaac    360
cagctagcgt gcaaggcgcc gcggctcagc gcgtaccggc gggcttcgaa accgcagtcc    420
tccggcgacc ccgaactccg ctccggagcc tcagccccct ggaaagtgat cccggcatcc    480
gagagccaag atg ccg gcc cac ttg ctg cag gac gat atc tct agc tcc     529
            Met Pro Ala His Leu Leu Gln Asp Asp Ile Ser Ser Ser
            1               5                   10 tat acc acc acc acc acc att aca gcg cct ccc tcc agg gtc ctg cag    577
Tyr Thr Thr Thr Thr Thr Ile Thr Ala Pro Pro Ser Arg Val Leu Gln
    15                  20                  25 aat gga gga gat aag ttg gag acg atg ccc ctc tac ttg gaa gac gac    625
Asn Gly Gly Asp Lys Leu Glu Thr Met Pro Leu Tyr Leu Glu Asp Asp
30                  35                  40                  45 att cgc cct gat ata aaa gat gat ata tat gac ccc acc tac aag gat    673
Ile Arg Pro Asp Ile Lys Asp Asp Ile Tyr Asp Pro Thr Tyr Lys Asp
                50                  55                  60 aag gaa ggc cca agc ccc aag gtt gaa tat gtc tgg aga aac atc atc    721
Lys Glu Gly Pro Ser Pro Lys Val Glu Tyr Val Trp Arg Asn Ile Ile
            65                  70                  75 ctt atg tct ctg cta cac ttg gga gcc ctg tat ggg atc act ttg att    769
Leu Met Ser Leu Leu His Leu Gly Ala Leu Tyr Gly Ile Thr Leu Ile
        80                  85                  90 cct acc tgc aag ttc tac acc tgg ctt tgg ggg gta ttc tac tat ttt    817
Pro Thr Cys Lys Phe Tyr Thr Trp Leu Trp Gly Val Phe Tyr Tyr Phe
    95                 100                 105 gtc agt gcc ctg ggc ata aca gca gga gct cat cgt ctg tgg agc cac    865
Val Ser Ala Leu Gly Ile Thr Ala Gly Ala His Arg Leu Trp Ser His
110                 115                 120                 125 cgc tct tac aaa gct cgg ctg ccc cta cgg ctc ttt ctg atc att gcc    913
Arg Ser Tyr Lys Ala Arg Leu Pro Leu Arg Leu Phe Leu Ile Ile Ala
                130                 135                 140 aac aca atg gca ttc cag aat gat gtc tat gaa tgg gct cgt gac cac    961
Asn Thr Met Ala Phe Gln Asn Asp Val Tyr Glu Trp Ala Arg Asp His
            145                 150                 155 cgt gcc cac cac aag ttt tca gaa aca cat gct gat cct cat aat tcc   1009
Arg Ala His His Lys Phe Ser Glu Thr His Ala Asp Pro His Asn Ser
        160                 165                 170 cga cgt ggc ttt ttc ttc tct cac gtg ggt tgg ctg ctt gtg cgc aaa   1057
Arg Arg Gly Phe Phe Phe Ser His Val Gly Trp Leu Leu Val Arg Lys
    175                 180                 185 cac cca gct gtc aaa gag aag ggg agt acg cta gac ttg tct gac cta   1105
```

|  |  |
|---|---|
| His Pro Ala Val Lys Glu Lys Gly Ser Thr Leu Asp Leu Ser Asp Leu<br>190                    195                    200                    205 |  |
| gaa gct gag aaa ctg gtg atg ttc cag agg agg tac tac aaa cct ggc<br>Glu Ala Glu Lys Leu Val Met Phe Gln Arg Arg Tyr Tyr Lys Pro Gly<br>                  210                    215                    220 | 1153 |
| ttg ctg atg atg tgc ttc atc ctg ccc acg ctt gtg ccc tgg tat ttc<br>Leu Leu Met Met Cys Phe Ile Leu Pro Thr Leu Val Pro Trp Tyr Phe<br>                225                    230                    235 | 1201 |
| tgg ggt gaa act ttt caa aac agt gtg ttc gtt gcc act ttc ttg cga<br>Trp Gly Glu Thr Phe Gln Asn Ser Val Phe Val Ala Thr Phe Leu Arg<br>        240                    245                    250 | 1249 |
| tat gct gtg gtg ctt aat gcc acc tgg ctg gtg aac agt gct gcc cac<br>Tyr Ala Val Val Leu Asn Ala Thr Trp Leu Val Asn Ser Ala Ala His<br>     255                    260                    265 | 1297 |
| ctc ttc gga tat cgt cct tat gac aag aac att agc ccc cgg gag aat<br>Leu Phe Gly Tyr Arg Pro Tyr Asp Lys Asn Ile Ser Pro Arg Glu Asn<br>270                    275                    280                    285 | 1345 |
| atc ctg gtt tca ctt gga gct gtg ggt gag ggc ttc cac aac tac cac<br>Ile Leu Val Ser Leu Gly Ala Val Gly Glu Gly Phe His Asn Tyr His<br>                  290                    295                    300 | 1393 |
| cac tcc ttt ccc tat gac tac tct gcc agt gag tac cgc tgg cac atc<br>His Ser Phe Pro Tyr Asp Tyr Ser Ala Ser Glu Tyr Arg Trp His Ile<br>                305                    310                    315 | 1441 |
| aac ttc acc aca ttc ttc att gat tgc atg gcc gcc ctc ggt ctg gcc<br>Asn Phe Thr Thr Phe Phe Ile Asp Cys Met Ala Ala Leu Gly Leu Ala<br>        320                    325                    330 | 1489 |
| tat gac cgg aag aaa gtc tcc aag gcc gcc atc ttg gcc agg att aaa<br>Tyr Asp Arg Lys Lys Val Ser Lys Ala Ala Ile Leu Ala Arg Ile Lys<br>    335                    340                    345 | 1537 |
| aga acc gga gat gga aac tac aag agt ggc tga gtttggggtc cctcaggttc<br>Arg Thr Gly Asp Gly Asn Tyr Lys Ser Gly<br>350                    355 | 1590 |
| ctttttcaaa aaccagccag gcagaggttt taatgtctgt ttattaacta ctgaataatg | 1650 |
| ctaccaggat gctaaagatg atgatgttaa cccattccag tacagtattc ttttaaaatt | 1710 |
| caaaagtatt gaaagccaac aactctgcct ttatgatgct aagctgatat tatttcttct | 1770 |
| cttatcctct ctctcttcta ggcccattgt cctccttttc actttattgc tatcgccctc | 1830 |
| ctttccctta ttgcctccca ggcaagcagc tggtcagtct ttgctcagtg tccagcttcc | 1890 |
| aaagcctaga caacctttct gtagcctaaa acgaatggtc tttgctccag ataactctct | 1950 |
| ttccttgagc tgttgtgagc tttgaagtag gtggcttgag ctagagataa aacagaatct | 2010 |
| tctgggtagt cccctgttga ttatcttcag cccaggcttt tgctagatgg aatgaaaaag | 2070 |
| caacttcatt tgacacaaag cttctaaagc aggtaaattg tcggggagag gagttagcat | 2130 |
| gtatgaatgt aaggatgagg gaagcgaagc aagaggaacc tctcgccatg atcagacata | 2190 |
| cagctgccta cctaatgagg acttcaagcc ccaccacata gcatgcttcc tttctctcct | 2250 |
| ggctcggggt aaaagtggc tgcggtgttt ggcaatgcta attcaatgcc gcaacatata | 2310 |
| gttgaggccg aggataaaga aaagacattt taagtttgta gtaaaagtgg tctctgctgg | 2370 |
| ggaagggttt tcttttcttt ttttctttaa taacaaggag atttcttagt tcatatatca | 2430 |
| agaagtcttg aagttgggtg tttccagaat tggtaaaaac agcagctcat agaatttga | 2490 |
| gtattccatg agctgctcat tacagttctt tcctctttct gctctgccat cttcaggata | 2550 |
| ttggttcttc ccctcatagt aataagatgg ctgtggcatt tccaaacatc caaaaaaagg | 2610 |
| gaaggattta aggaggtgaa gtcgggtcaa aaataaaata tatatacata tatacattgc | 2670 |

-continued

```
ttagaacgtt aaactattag agtatttccc ttccaaagag ggatgtttgg aaaaaactct    2730
gaaggagagg aggaattagt tgggatgcca atttcctctc cactgctgga catgagatgg    2790
agaggctgag ggacaggatc tataggcagc ttctaagagc gaacttcaca taggaaggga    2850
tctgagaaca cgttgccagg ggcttgagaa ggttactgag tgagttattg ggagtcttaa    2910
taaaataaac tagatattag gtccattcat taattagttc cagtttctcc ttgaaatgag    2970
taaaaactag aaggcttctc tccacagtgt tgtgcccctt cactcatttt tttttgagga    3030
gaagggggtc tctgttaaca tctagcctaa agtatacaac tgcctggggg cagggttag    3090
gaatctcttc actaccctga ttcttgattc ctggctctac cctgtctgtc ccttttcttt    3150
gaccagatct ttctcttccc tgaacgtttt cttctttccc tggacaggca gcctcctttg    3210
tgtgtattca gaggcagtga tgacttgctg tccaggcagc tccctcctgc acacagaatg    3270
ctcagggtca ctgaaccact gcttctcttt tgaaagtaga gctagctgcc actttcacgt    3330
ggcctccgca gtgtctccac ctacacccct gtgctcccct gccacactga tggctcaaga    3390
caaggctggc aaaccctccc agaaacatct ctggcccaga aagcctctct ctccctccct    3450
ctctcatgag gcacagccaa gccaagcgct catgttgagc cagtgggcca gccacagagc    3510
aaaagagggt ttatttttcag tcccctctct ctgggtcaga accagagggc atgctgaatg    3570
cccctgctt acttggtgag ggtgccccgc ctgagtcagt gctctcagct ggcagtgcaa    3630
tgcttgtaga agtaggagga aacagttctc actgggaaga agcaagggca agaacccaag    3690
tgcctcacct cgaaggaggg ccctgttccc tggagtcagg gtgaactgca agctttggc    3750
tgagacctgg gatttgagat accacaaacc ctgctgaaca cagtgtctgt tcagcaaact    3810
aaccagcatt ccctacagcc tagggcagac aatagtatag aagtctggaa aaaaacaaaa    3870
acagaatttg agaaccttgg accactcctg tccctgtagc tcagtcatca aagcagaagt    3930
ctggctttgc tctattaaga ttggaaatgt acactaccaa acactcagtc cactgttgag    3990
ccccagtgct ggaagggagg aaggcctttc ttctgtgtta attgcgtaga ggctacaggg    4050
gttagcctgg actaaaggca tccttgtctt ttgagctatt caccctcagta gaaaaggatc    4110
taagggaaga tcactgtagt ttagttctgt tgacctgtgc acctacccct tggaaatgtc    4170
tgctggtatt tctaattcca caggtcatca gatgcctgct tgataatata taaacaataa    4230
aaacaacttt cacttcttcc tattgtaatc gtgtgccatg gatctgatct gtaccatgac    4290
cctacataag gctggatggc acctcaggct gagggcccca atgtatgtgt ggctgtgggt    4350
gtgggtggga gtgtgtctgc tgagtaagga acacgatttt caagattcta aagctcaatt    4410
caagtgacac attaatgata aactcagatc tgatcaagag tccggatttc taacagtcct    4470
tgctttgggg ggtgtgctga caacttagct caggtgcctt acatcttttc taatcacagt    4530
gttgcatatg agcctgccct cactccctct gcagaatccc tttgcacctg agaccctact    4590
gaagtggctg gtagaaaaag gggcctgagt ggaggattat cagtatcacg atttgcagga    4650
ttcccttctg ggcttcattc tggaaacttt tgttagggct gcttttctta agtgcccaca    4710
tttgatggag ggtggaaata atttgaatgt atttgattta aagttttttt tttttttttt    4770
gggttaaaag atggttgtag catttaaaat ggaaaatttt ctccttggtt tgctagtatc    4830
ttgggtgtat tctctgtaag tgtagctcaa ataggtcatc atgaaaggtt aaaaaagcga    4890
ggtggccatg ttatgctggt ggttaaggcc agggcctctc caaccactgt gccactgact    4950
tgctgtgtga ccctgggcaa gtcacttaac tataaggtgc ctcagttttc cttcgttaa    5010
aatggggata ataatactga cctaccctcaa agggcagttt tgaggcatga ctaatgcttt    5070
```

```
ttagaaagca ttttgggatc cttcagcaca ggaattctca agacctgagt atttttata    5130 ataggaatgt ccaccatgaa cttgatacgt ccgtgtgtcc cagatgctgt cattagtcta    5190
tatggttctc caagaaactg aatgaatcca ttggagaagc ggtggataac tagccagaca    5250
aaatttgaga atacataaac aacgcattgc cacggaaaca tacagaggat gccttttctg    5310
tgattgggtg ggattttttc cctttttatg tgggatatag tagttacttg tgacaagaat    5370
aattttggaa taatttctat taatatcaac tctgaagcta attgtactaa tctgagattg    5430
tgtttgttca aataaaagt gaagtgaatc tgattgcaaa aaa    5473

<210> SEQ ID NO 2
<211> LENGTH: 359
<212> TYPE: PRT
<213> ORGANISM: Homo sapiens

<400> SEQUENCE: 2

Met Pro Ala His Leu Leu Gln Asp Asp Ile Ser Ser Ser Tyr Thr Thr
1               5                   10                  15

Thr Thr Thr Ile Thr Ala Pro Pro Ser Arg Val Leu Gln Asn Gly Gly
            20                  25                  30

Asp Lys Leu Glu Thr Met Pro Leu Tyr Leu Glu Asp Ile Arg Pro
        35                  40                  45

Asp Ile Lys Asp Ile Tyr Asp Pro Thr Tyr Lys Asp Lys Glu Gly
    50                  55                  60

Pro Ser Pro Lys Val Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
                85                  90                  95

Lys Phe Tyr Thr Trp Leu Trp Gly Val Phe Tyr Tyr Phe Val Ser Ala
            100                 105                 110

Leu Gly Ile Thr Ala Gly Ala His Arg Leu Trp Ser His Arg Ser Tyr
        115                 120                 125

Lys Ala Arg Leu Pro Leu Arg Leu Phe Leu Ile Ile Ala Asn Thr Met
    130                 135                 140

Ala Phe Gln Asn Asp Val Tyr Glu Trp Ala Arg Asp His Arg Ala His
145                 150                 155                 160

His Lys Phe Ser Glu Thr His Ala Asp Pro His Asn Ser Arg Arg Gly
                165                 170                 175

Phe Phe Phe Ser His Val Gly Trp Leu Leu Val Arg Lys His Pro Ala
            180                 185                 190

Val Lys Glu Lys Gly Ser Thr Leu Asp Leu Ser Asp Leu Glu Ala Glu
        195                 200                 205

Lys Leu Val Met Phe Gln Arg Arg Tyr Tyr Lys Pro Gly Leu Leu Met
    210                 215                 220

Met Cys Phe Ile Leu Pro Thr Leu Val Pro Trp Tyr Phe Trp Gly Glu
225                 230                 235                 240

Thr Phe Gln Asn Ser Val Phe Val Ala Thr Phe Leu Arg Tyr Ala Val
                245                 250                 255

Val Leu Asn Ala Thr Trp Leu Val Asn Ser Ala Ala His Leu Phe Gly
            260                 265                 270

Tyr Arg Pro Tyr Asp Lys Asn Ile Ser Pro Arg Glu Asn Ile Leu Val
        275                 280                 285

Ser Leu Gly Ala Val Gly Glu Gly Phe His Asn Tyr His His Ser Phe
    290                 295                 300
```

```
Pro Tyr Asp Tyr Ser Ala Ser Glu Tyr Arg Trp His Ile Asn Phe Thr
305                 310                 315                 320

Thr Phe Phe Ile Asp Cys Met Ala Ala Leu Gly Leu Ala Tyr Asp Arg
                325                 330                 335

Lys Lys Val Ser Lys Ala Ala Ile Leu Ala Arg Ile Lys Arg Thr Gly
            340                 345                 350

Asp Gly Asn Tyr Lys Ser Gly
            355

<210> SEQ ID NO 3
<211> LENGTH: 9
<212> TYPE: PRT
<213> ORGANISM: Homo sapiens

<400> SEQUENCE: 3

Lys Leu Glu Thr Met Pro Leu Tyr Leu
1               5

<210> SEQ ID NO 4
<211> LENGTH: 10
<212> TYPE: PRT
<213> ORGANISM: Homo sapiens

<400> SEQUENCE: 4

Tyr Leu Glu Asp Asp Ile Arg Pro Asp Ile
1               5                   10

<210> SEQ ID NO 5
<211> LENGTH: 9
<212> TYPE: PRT
<213> ORGANISM: Homo sapiens

<400> SEQUENCE: 5

Tyr Val Trp Arg Asn Ile Ile Leu Met
1               5

<210> SEQ ID NO 6
<211> LENGTH: 10
<212> TYPE: PRT
<213> ORGANISM: Homo sapiens

<400> SEQUENCE: 6

Ile Leu Met Ser Leu Leu His Leu Gly Ala
1               5                   10

<210> SEQ ID NO 7
<211> LENGTH: 10
<212> TYPE: PRT
<213> ORGANISM: Homo sapiens

<400> SEQUENCE: 7

Leu Leu His Leu Gly Ala Leu Tyr Gly Ile
1               5                   10

<210> SEQ ID NO 8
<211> LENGTH: 10
<212> TYPE: PRT
<213> ORGANISM: Homo sapiens

<400> SEQUENCE: 8

Ala Leu Tyr Gly Ile Thr Leu Ile Pro Thr
1               5                   10
```

```
<210> SEQ ID NO 9
<211> LENGTH: 10
<212> TYPE: PRT
<213> ORGANISM: Homo sapiens

<400> SEQUENCE: 9

Thr Leu Ile Pro Thr Cys Lys Phe Tyr Thr
1               5                   10

<210> SEQ ID NO 10
<211> LENGTH: 10
<212> TYPE: PRT
<213> ORGANISM: Homo sapiens

<400> SEQUENCE: 10

Trp Leu Trp Gly Val Phe Tyr Tyr Phe Val
1               5                   10

<210> SEQ ID NO 11
<211> LENGTH: 10
<212> TYPE: PRT
<213> ORGANISM: Homo sapiens

<400> SEQUENCE: 11

Gly Val Phe Tyr Tyr Phe Val Ser Ala Leu
1               5                   10

<210> SEQ ID NO 12
<211> LENGTH: 10
<212> TYPE: PRT
<213> ORGANISM: Homo sapiens

<400> SEQUENCE: 12

Arg Leu Trp Ser His Arg Ser Tyr Lys Ala
1               5                   10

<210> SEQ ID NO 13
<211> LENGTH: 9
<212> TYPE: PRT
<213> ORGANISM: Homo sapiens

<400> SEQUENCE: 13

Arg Leu Pro Leu Arg Leu Phe Leu Ile
1               5

<210> SEQ ID NO 14
<211> LENGTH: 9
<212> TYPE: PRT
<213> ORGANISM: Homo sapiens

<400> SEQUENCE: 14

Arg Leu Phe Leu Ile Ile Ala Asn Thr
1               5

<210> SEQ ID NO 15
<211> LENGTH: 9
<212> TYPE: PRT
<213> ORGANISM: Homo sapiens

<400> SEQUENCE: 15

Phe Leu Ile Ile Ala Asn Thr Met Ala
1               5

<210> SEQ ID NO 16
```

```
<211> LENGTH: 10
<212> TYPE: PRT
<213> ORGANISM: Homo sapiens

<400> SEQUENCE: 16

Trp Leu Leu Val Arg Lys His Pro Ala Val
1               5                   10

<210> SEQ ID NO 17
<211> LENGTH: 9
<212> TYPE: PRT
<213> ORGANISM: Homo sapiens

<400> SEQUENCE: 17

Gly Leu Leu Met Met Cys Phe Ile Leu
1               5

<210> SEQ ID NO 18
<211> LENGTH: 11
<212> TYPE: PRT
<213> ORGANISM: Homo sapiens

<400> SEQUENCE: 18

Leu Leu Met Met Cys Phe Ile Leu Pro Thr Leu
1               5                   10

<210> SEQ ID NO 19
<211> LENGTH: 10
<212> TYPE: PRT
<213> ORGANISM: Homo sapiens

<400> SEQUENCE: 19

Phe Val Ala Thr Phe Leu Arg Tyr Ala Val
1               5                   10

<210> SEQ ID NO 20
<211> LENGTH: 9
<212> TYPE: PRT
<213> ORGANISM: Homo sapiens

<400> SEQUENCE: 20

Val Val Leu Asn Ala Thr Trp Leu Val
1               5

<210> SEQ ID NO 21
<211> LENGTH: 9
<212> TYPE: PRT
<213> ORGANISM: Homo sapiens

<400> SEQUENCE: 21

Trp Leu Val Asn Ser Ala Ala His Leu
1               5

<210> SEQ ID NO 22
<211> LENGTH: 9
<212> TYPE: PRT
<213> ORGANISM: Homo sapiens

<400> SEQUENCE: 22

His Ile Asn Phe Thr Thr Phe Phe Ile
1               5

<210> SEQ ID NO 23
<211> LENGTH: 10
<212> TYPE: PRT
```

<213> ORGANISM: Homo sapiens

<400> SEQUENCE: 23

Phe Ile Asp Cys Met Ala Ala Leu Gly Leu
1               5                   10

<210> SEQ ID NO 24
<211> LENGTH: 10
<212> TYPE: PRT
<213> ORGANISM: Homo sapiens

<400> SEQUENCE: 24

Lys Phe Tyr Thr Trp Leu Trp Gly Val Phe
1               5                   10

<210> SEQ ID NO 25
<211> LENGTH: 10
<212> TYPE: PRT
<213> ORGANISM: Homo sapiens

<400> SEQUENCE: 25

Thr Trp Leu Trp Gly Val Phe Tyr Tyr Phe
1               5                   10

<210> SEQ ID NO 26
<211> LENGTH: 10
<212> TYPE: PRT
<213> ORGANISM: Homo sapiens

<400> SEQUENCE: 26

Phe Tyr Tyr Phe Val Ser Ala Leu Gly Ile
1               5                   10

<210> SEQ ID NO 27
<211> LENGTH: 10
<212> TYPE: PRT
<213> ORGANISM: Homo sapiens

<400> SEQUENCE: 27

Ser Tyr Lys Ala Arg Leu Pro Leu Arg Leu
1               5                   10

<210> SEQ ID NO 28
<211> LENGTH: 9
<212> TYPE: PRT
<213> ORGANISM: Homo sapiens

<400> SEQUENCE: 28

Phe Phe Ser His Val Gly Trp Leu Leu
1               5

<210> SEQ ID NO 29
<211> LENGTH: 10
<212> TYPE: PRT
<213> ORGANISM: Homo sapiens

<400> SEQUENCE: 29

Leu Met Met Cys Phe Ile Leu Pro Thr Leu
1               5                   10

<210> SEQ ID NO 30
<211> LENGTH: 9
<212> TYPE: PRT
<213> ORGANISM: Homo sapiens

-continued

<400> SEQUENCE: 30

Pro Trp Tyr Phe Trp Gly Glu Thr Phe
1               5

<210> SEQ ID NO 31
<211> LENGTH: 10
<212> TYPE: PRT
<213> ORGANISM: Homo sapiens

<400> SEQUENCE: 31

Arg Tyr Ala Val Val Leu Asn Ala Thr Trp
1               5                   10

<210> SEQ ID NO 32
<211> LENGTH: 9
<212> TYPE: PRT
<213> ORGANISM: Homo sapiens

<400> SEQUENCE: 32

Gly Tyr Arg Pro Tyr Asp Lys Asn Ile
1               5

<210> SEQ ID NO 33
<211> LENGTH: 9
<212> TYPE: PRT
<213> ORGANISM: Homo sapiens

<400> SEQUENCE: 33

Gly Phe His Asn Tyr His His Ser Phe
1               5

<210> SEQ ID NO 34
<211> LENGTH: 10
<212> TYPE: PRT
<213> ORGANISM: Homo sapiens

<400> SEQUENCE: 34

Asn Tyr His His Ser Phe Pro Tyr Asp Tyr
1               5                   10

<210> SEQ ID NO 35
<211> LENGTH: 9
<212> TYPE: PRT
<213> ORGANISM: Homo sapiens

<400> SEQUENCE: 35

Asp Tyr Ser Ala Ser Glu Tyr Arg Trp
1               5

<210> SEQ ID NO 36
<211> LENGTH: 9
<212> TYPE: PRT
<213> ORGANISM: Homo sapiens

<400> SEQUENCE: 36

Arg Trp His Ile Asn Phe Thr Thr Phe
1               5

<210> SEQ ID NO 37
<211> LENGTH: 24
<212> TYPE: PRT
<213> ORGANISM: Homo sapiens

<400> SEQUENCE: 37

```
Val Glu Tyr Val Trp Arg Asn Ile Ile Leu Met Ser Leu Leu His Leu
1               5                   10                  15

Gly Ala Leu Tyr Gly Ile Thr Leu
            20
```

<210> SEQ ID NO 38
<211> LENGTH: 18
<212> TYPE: PRT
<213> ORGANISM: Homo sapiens

<400> SEQUENCE: 38

```
Trp Gly Val Phe Tyr Tyr Phe Val Ser Ala Leu Gly Ile Thr Ala Gly
1               5                   10                  15

Ala His
```

<210> SEQ ID NO 39
<211> LENGTH: 20
<212> TYPE: PRT
<213> ORGANISM: Homo sapiens

<400> SEQUENCE: 39

```
Thr Ala Gly Ala His Arg Leu Trp Ser His Arg Ser Tyr Lys Ala Arg
1               5                   10                  15

Leu Pro Leu Arg
            20
```

<210> SEQ ID NO 40
<211> LENGTH: 15
<212> TYPE: PRT
<213> ORGANISM: Homo sapiens

<400> SEQUENCE: 40

```
His Arg Ser Tyr Lys Ala Arg Leu Pro Leu Arg Leu Phe Leu Ile
1               5                   10                  15
```

<210> SEQ ID NO 41
<211> LENGTH: 16
<212> TYPE: PRT
<213> ORGANISM: Homo sapiens

<400> SEQUENCE: 41

```
Pro Leu Arg Leu Phe Leu Ile Ile Ala Asn Thr Met Ala Phe Gln Asn
1               5                   10                  15
```

<210> SEQ ID NO 42
<211> LENGTH: 15
<212> TYPE: PRT
<213> ORGANISM: Homo sapiens

<400> SEQUENCE: 42

```
His Val Gly Trp Leu Leu Val Arg Lys His Pro Ala Val Lys Glu
1               5                   10                  15
```

<210> SEQ ID NO 43
<211> LENGTH: 17
<212> TYPE: PRT
<213> ORGANISM: Homo sapiens

<400> SEQUENCE: 43

```
Ala Glu Lys Leu Val Met Phe Gln Arg Arg Tyr Tyr Lys Pro Gly Leu
1               5                   10                  15

Leu
```

<210> SEQ ID NO 44
<211> LENGTH: 16
<212> TYPE: PRT
<213> ORGANISM: Homo sapiens

<400> SEQUENCE: 44

Asn Ala Thr Trp Leu Val Asn Ser Ala Ala His Leu Phe Gly Tyr Arg
1               5                   10                  15

<210> SEQ ID NO 45
<211> LENGTH: 12
<212> TYPE: PRT
<213> ORGANISM: Homo sapiens

<400> SEQUENCE: 45

Ala Ser Glu Tyr Arg Trp His Ile Asn Phe Thr Thr
1               5                   10

<210> SEQ ID NO 46
<211> LENGTH: 9
<212> TYPE: PRT
<213> ORGANISM: Artificial
<220> FEATURE:
<223> OTHER INFORMATION: A2-control peptide

<400> SEQUENCE: 46

Ser Leu Tyr Asn Thr Tyr Ala Thr Leu
1               5

<210> SEQ ID NO 47
<211> LENGTH: 9
<212> TYPE: PRT
<213> ORGANISM: Artificial
<220> FEATURE:
<223> OTHER INFORMATION: A24-control peptide

<400> SEQUENCE: 47

Arg Tyr Leu Arg Asp Gln Gln Leu Leu
1               5

<210> SEQ ID NO 48
<211> LENGTH: 18
<212> TYPE: PRT
<213> ORGANISM: Artificial
<220> FEATURE:
<223> OTHER INFORMATION: Helper-control peptide

<400> SEQUENCE: 48

Tyr Val Asp Arg Phe Phe Lys Thr Leu Arg Ala Glu Gln Ala Thr Gln
1               5                   10                  15

Asp Val

<210> SEQ ID NO 49
<211> LENGTH: 20
<212> TYPE: DNA
<213> ORGANISM: Artificial
<220> FEATURE:
<223> OTHER INFORMATION: primer sense

<400> SEQUENCE: 49
gatgatgtgc ttcatcctgc                                              20

<210> SEQ ID NO 50
<211> LENGTH: 20
<212> TYPE: DNA

```
<213> ORGANISM: Artificial
<220> FEATURE:
<223> OTHER INFORMATION: primer antisense

<400> SEQUENCE: 50
tgtggtgaag ttgatgtgcc                                              20

<210> SEQ ID NO 51
<211> LENGTH: 18
<212> TYPE: DNA
<213> ORGANISM: Artificial
<220> FEATURE:
<223> OTHER INFORMATION: GAPDH primer

<400> SEQUENCE: 51
gggctgcttt taactctg                                                18

<210> SEQ ID NO 52
<211> LENGTH: 18
<212> TYPE: DNA
<213> ORGANISM: Artificial
<220> FEATURE:
<223> OTHER INFORMATION: GAPDH primer

<400> SEQUENCE: 52
ccaggaaatg agcttgac                                                18
```